US012729401B2

(12) United States Patent
Hacohen et al.

(10) Patent No.: US 12,729,401 B2
(45) Date of Patent: Sep. 8, 2026

(54) CHIMERIC AMPLICON ARRAY SEQUENCING

(71) Applicants: THE BROAD INSTITUTE, INC., Cambridge, MA (US); MASSACHUSETTS INSTITUTE OF TECHNOLOGY, Cambridge, MA (US); THE GENERAL HOSPITAL CORPORATION, Boston, MA (US)

(72) Inventors: Nir Hacohen, Boston, MA (US); Aziz Al'Khafaji, Cambridge, MA (US); Paul Blainey, Cambridge, MA (US); Mehrtash Babadi, Cambridge, MA (US); Kiran V Garimella, Cambridge, MA (US); Jonathan Theodore Smith, Cambridge, MA (US)

(73) Assignees: THE BROAD INSTITUTE, INC., Cambridge, MA (US); MASSACHUSETTS INSTITUTE OF TECHNOLOGY, Cambridge, MA (US); THE GENERAL HOSPITAL CORPORATION, Boston, MA (US)

( * ) Notice: Subject to any disclaimer, the term of this patent is extended or adjusted under 35 U.S.C. 154(b) by 757 days.

(21) Appl. No.: 18/001,649

(22) PCT Filed: Jun. 14, 2021

(86) PCT No.: PCT/US2021/037226

§ 371 (c)(1),
(2) Date: Dec. 13, 2022

(87) PCT Pub. No.: WO2021/257453

PCT Pub. Date: Dec. 23, 2021

(65) Prior Publication Data

US 2023/0235394 A1 Jul. 27, 2023

Related U.S. Application Data

(60) Provisional application No. 63/039,004, filed on Jun. 15, 2020.

(51) Int. Cl.
*C12Q 1/68* (2018.01)
*C12Q 1/6874* (2018.01)
*C12Q 1/6806* (2018.01)

(52) U.S. Cl.
CPC ......... *C12Q 1/6874* (2013.01); *C12Q 1/6806* (2013.01); *C12Q 2600/16* (2013.01)

(58) Field of Classification Search
CPC .................................................... C12Q 1/6869
See application file for complete search history.

(56) References Cited

U.S. PATENT DOCUMENTS

2009/0009903 A1 1/2009 Lee et al.
2010/0105052 A1 4/2010 Drmanac et al.
(Continued)

FOREIGN PATENT DOCUMENTS

CN 104946737 A 9/2015
WO 20080133643 A2 11/2008
WO 20180227025 A1 12/2018

OTHER PUBLICATIONS

Prabakar et al., Genome Biology 20:134, 1-9 (2019 (Year: 2019).*
(Continued)

*Primary Examiner* — Kenneth R Horlick
(74) *Attorney, Agent, or Firm* — FIG. 1 Patents

(57) ABSTRACT

The present disclosure relates to compositions and methods for nucleic acid sequencing, and specifically, at least in certain aspects, provides methods and compositions for enhancing the efficacy, throughput and/or yield of known long-range sequencing platforms, by providing chimeric arrays of input sequences. Such arrays of component nucleic
(Continued)

acid sequence elements can be prepared via methods that minimize introduction of bias. The application of the current methods to obtain isoform sequencing information, e.g., from patient samples is specifically also provided, as are methods for mitochondrial lineage tracing that employ the instant chimeric amplicon sequencing processes. Methods and systems for array nucleic acid sequence processing and interpretation are also provided.

20 Claims, 19 Drawing Sheets

Specification includes a Sequence Listing.

(56) References Cited

U.S. PATENT DOCUMENTS

| | | | | |
|---|---|---|---|---|
| 2016/0026495 | A1 | 1/2016 | Upadrasta et al. | |
| 2016/0264958 | A1 | 9/2016 | Toro et al. | |
| 2018/0148757 | A1* | 5/2018 | Mitra | C12Q 1/6853 |
| 2019/0194648 | A1* | 6/2019 | Wang | C40B 50/06 |

OTHER PUBLICATIONS

CN First Office Action corresponding to Application No. 202180050335.2, dated May 28, 2025, 8 pages.
CN First Office Action Search Report corresponding to Application No. 202180050335.2, dated May 28, 2025, 2 pages.
Zheng, Ying-Feng et al., "HIT-scISOseq: High-throughput and High-accuracy Single-cell Full-length Isoform Sequencing for Corneal Epithelium", bioRXIV, 2020, 21 pages.
Search Report and Written Opinion dated Dec. 8, 2021 in PCT/US2021/037226.
Gibson et al. Enzymatic assembly of DNA molecules up to several hundred kilobases. Nature Methods. May 2009, vol. 6, No. 5, p. 343-345; especially abstract; Figure 1.
Extended European Search Report in corresponding EP application No. 21826447.1 dated Oct. 2, 2024.
Partial Supplementary European Search Report in corresponding EP application No. 21826447.1 dated Jul. 11, 2024.
International Preliminary Report on Patentability mailed Dec. 29, 2022 in International Application No. PCTUS2021/037226.
Foreign Office Action issued in JP 2023521274, mailed Jul. 3, 2025, 10 pages.
Foreign Office Action issued in CN Application No. 202180050335.2, mailed Mar. 23, 2026, 24 pages.
Foreign Office Action issued in JP 2023-521274, mailed Apr. 23, 2019, 8 pages.

* cited by examiner

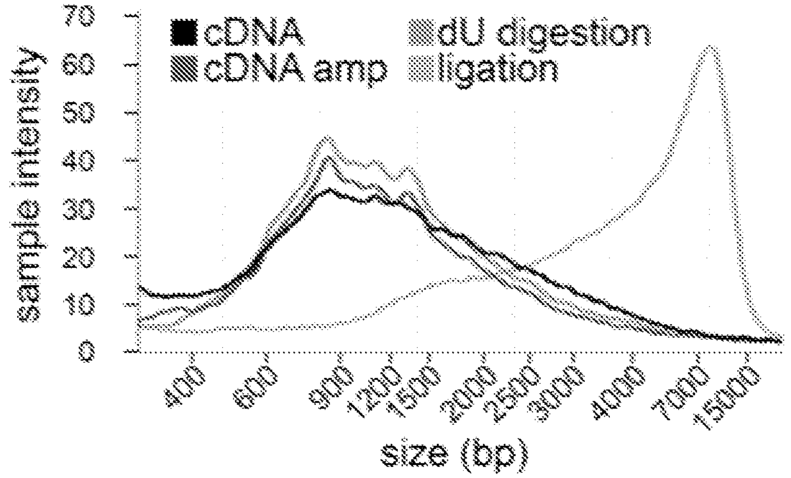
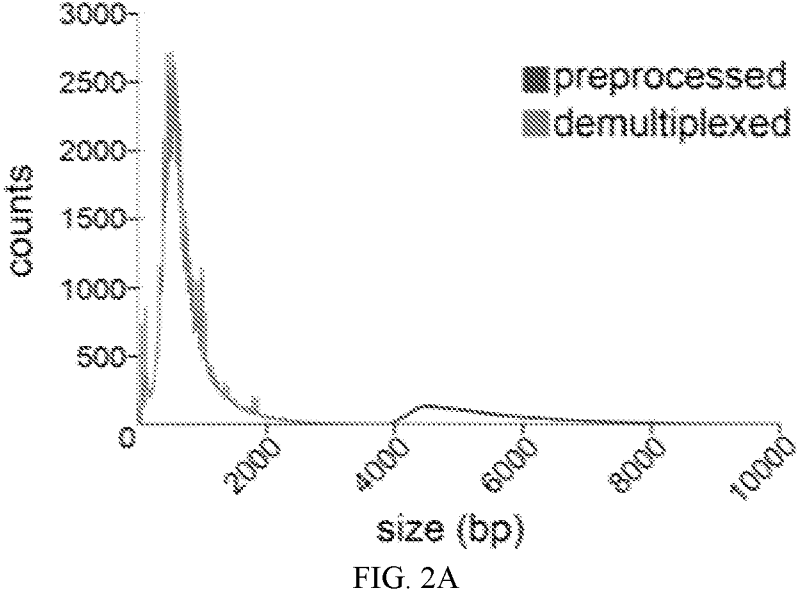
FIG. 2A

FIG. 5

| | Ligation Profile | Length | Count | Percent of Total Counts |
|---|---|---|---|---|
| 0 | A B C D E F G H I J K L M N O P | 16 | 484869 | 29.88% |
| 1 | A' B' C' D' E' F' G' H' I' J' K' L' M' N' O' P' | 16 | 476205 | 29.34% |
| 2 | C' D' E' F' G' H' I' J' K' L' M' N' O' P' | 14 | 54879 | 3.38% |
| 3 | C D E F G H I J K L M N O P | 14 | 54471 | 3.36% |
| 4 | A B C D E F G H I J K L M N | 14 | 49074 | 3.02% |
| 5 | A B C D E F G H I J K L M | 13 | 46094 | 2.84% |
| 6 | A' B' C' D' E' F' G' H' I' J' K' L' M' N' | 14 | 40890 | 2.52% |
| 7 | A' B' C' D' E' F' G' H' I' J' K' L' M' | 13 | 39838 | 2.45% |
| 8 | A B C D E F G H I J K L | 12 | 31918 | 1.97% |
| 9 | D' E' F' G' H' I' J' K' L' M' N' O' P' | 13 | 30846 | 1.90% |
| 10 | D E F G H I J K L M N O P | 13 | 29839 | 1.84% |
| 11 | A' B' C' D' E' F' G' H' I' J' K' L' | 12 | 28700 | 1.77% |
| 12 | E' F' G' H' I' J' K' L' M' N' O' P' | 12 | 28590 | 1.76% |
| 13 | E F G H I J K L M N O P | 12 | 28128 | 1.73% |
| 14 | A B C D E F G H I J K | 11 | 14138 | 0.87% |
| 15 | A B C D E F G H I J K L M N O | 15 | 13311 | 0.82% |
| 16 | B' C' D' E' F' G' H' I' J' K' L' M' N' O' P' | 15 | 12297 | 0.76% |
| 17 | A' B' C' D' E' F' G' H' I' J' K' | 11 | 11336 | 0.70% |
| 18 | A' B' C' D' E' F' G' H' I' J' K' L' M' N' O' | 15 | 10711 | 0.66% |
| 19 | B C D E F G H I J K L M N O P | 15 | 10495 | 0.65% |

FIG. 7

| Number of HiFi Reads | Number of Chimeric Amplicon Array Sequencing Reads | Number of Chimeric Amplicon Array Sequencing Reads Reclaimed by Current Read Analysis Methods | Total Number of Chimeric Amplicon Array Sequencing Reads | Total Chimeric Amplicon Array Sequencing Yield Increase |
|---|---|---|---|---|
| 2477400 | 29789780 | 10194059 | 39983839 | 16.14x |
| 1622783 | 22662840 | 12794497 | 35457337 | 21.84x |

FIG. 8

SEQUENCE LISTING

<160> NUMBER OF SEQ ID NOS: 18

<210> SEQ ID NO 1
<211> LENGTH: 15
<212> TYPE: DNA
<213> ORGANISM: Artificial
<220> FEATURE:
<223> OTHER INFORMATION: synthetic

<400> SEQUENCE: 1
agcaccataa tgtgt 15

<210> SEQ ID NO 2
<211> LENGTH: 15
<212> TYPE: DNA
<213> ORGANISM: Artificial
<220> FEATURE:
<223> OTHER INFORMATION: synthetic

<400> SEQUENCE: 2
cttgtaagct gtcta 15

<210> SEQ ID NO 3
<211> LENGTH: 15
<212> TYPE: DNA
<213> ORGANISM: Artificial
<220> FEATURE:
<223> OTHER INFORMATION: synthetic

<400> SEQUENCE: 3
ctctgtcagg tccga 15

<210> SEQ ID NO 4
<211> LENGTH: 15
<212> TYPE: DNA
<213> ORGANISM: Artificial
<220> FEATURE:
<223> OTHER INFORMATION: synthetic

<400> SEQUENCE: 4
cctcctcctc cagaa 15

<210> SEQ ID NO 5
<211> LENGTH: 15
<212> TYPE: DNA
<213> ORGANISM: Artificial
<220> FEATURE:
<223> OTHER INFORMATION: synthetic

<400> SEQUENCE: 5
tcgctggtat tccaa 15

<210> SEQ ID NO 6
<211> LENGTH: 15
<212> TYPE: DNA
<213> ORGANISM: Artificial
<220> FEATURE:
<223> OTHER INFORMATION: synthetic

<400> SEQUENCE: 6
gcttacttgt gaaga 15

<210> SEQ ID NO 7
<211> LENGTH: 15
<212> TYPE: DNA
<213> ORGANISM: Artificial

<220> FEATURE:
<223> OTHER INFORMATION: synthetic

<400> SEQUENCE: 7
taaccgtatg gttga 15

<210> SEQ ID NO 8
<211> LENGTH: 15
<212> TYPE: DNA
<213> ORGANISM: Artificial
<220> FEATURE:
<223> OTHER INFORMATION: synthetic

<400> SEQUENCE: 8
gatggcgcta tctca 15

<210> SEQ ID NO 9
<211> LENGTH: 15
<212> TYPE: DNA
<213> ORGANISM: Artificial
<220> FEATURE:
<223> OTHER INFORMATION: synthetic

<400> SEQUENCE: 9
ctaccagtga ggaag 15

<210> SEQ ID NO 10
<211> LENGTH: 15
<212> TYPE: DNA
<213> ORGANISM: Artificial
<220> FEATURE:
<223> OTHER INFORMATION: synthetic

<400> SEQUENCE: 10
gagtccaatt cgcag 15

<210> SEQ ID NO 11
<211> LENGTH: 15
<212> TYPE: DNA
<213> ORGANISM: Artificial
<220> FEATURE:
<223> OTHER INFORMATION: synthetic

<400> SEQUENCE: 11
atcaaggctt aacgg 15

<210> SEQ ID NO 12
<211> LENGTH: 15
<212> TYPE: DNA
<213> ORGANISM: Artificial
<220> FEATURE:
<223> OTHER INFORMATION: synthetic

<400> SEQUENCE: 12
tgttgaatcc tagcg 15

<210> SEQ ID NO 13
<211> LENGTH: 15
<212> TYPE: DNA
<213> ORGANISM: Artificial
<220> FEATURE:
<223> OTHER INFORMATION: synthetic

<400> SEQUENCE: 13
gtgcgttgcg aattg 15

```
<210> SEQ ID NO 14
<211> LENGTH: 15
<212> TYPE: DNA
<213> ORGANISM: Artificial
<220> FEATURE:
<223> OTHER INFORMATION: synthetic

<400> SEQUENCE: 14

cggtaatgta ccggc                                                    15


<210> SEQ ID NO 15
<211> LENGTH: 15
<212> TYPE: DNA
<213> ORGANISM: Artificial
<220> FEATURE:
<223> OTHER INFORMATION: synthetic

<400> SEQUENCE: 15

attgcgtagt tggcc                                                    15


<210> SEQ ID NO 16
<211> LENGTH: 15
<212> TYPE: DNA
<213> ORGANISM: Artificial
<220> FEATURE:
<223> OTHER INFORMATION: synthetic

<400> SEQUENCE: 16

cacttggtcg caatc                                                    15


<210> SEQ ID NO 17
<211> LENGTH: 15
<212> TYPE: DNA
<213> ORGANISM: Artificial
<220> FEATURE:
<223> OTHER INFORMATION: synthetic

<400> SEQUENCE: 17

gtaagccttc gtgtc                                                    15


<210> SEQ ID NO 18
<211> LENGTH: 15
<212> TYPE: DNA
<213> ORGANISM: Artificial
<220> FEATURE:
<223> OTHER INFORMATION: synthetic

<400> SEQUENCE: 18

cctagatcag agcct                                                    15
```

CHIMERIC AMPLICON ARRAY SEQUENCING

CROSS REFERENCE TO RELATED APPLICATIONS

This application is a national stage application, filed under 35 U.S.C. § 371, of International Application No. PCT/US2021/037226, filed Jun. 14, 2021, which claims priority to U.S. Provisional Application No. 63/039,004, filed Jun. 15, 2020, entitled "Chimeric Amplicon Array Sequencing." The entire contents of the aforementioned applications are incorporated herein by reference.

STATEMENT REGARDING FEDERALLY SPONSORED RESEARCH

This invention was made with government support under Grant No. U19AI082630 awarded by the National Institutes of Health. The government has certain rights in the invention.

SEQUENCE LISTING

The instant application contains a Sequence Listing which has been filed electronically in ASCII format and is hereby incorporated by reference in its entirety. Said ASCII copy, created on Dec. 14, 2022, is named BN00007_1182_BI_10723_SL.txt and is 4 KB in size.

FIELD OF THE INVENTION

The invention relates generally to methods and compositions for nucleic acid sequencing, particularly to preparation of nucleic acid populations for sequencing.

BACKGROUND OF THE INVENTION

While the advent of next generation DNA sequencing has revolutionized biological research, there are a number of key genetic features that remain poorly resolved by current sequencing platforms. For example, alternative splicing, a core biological process that enables profound and essential diversification of gene function through differential splicing of exons during mRNA maturation is insufficiently captured via known single-cell sequencing methods. For the study of tumor clonal evolution, the capacity to derive clonal relationships from marker alleles from single cells requires robust sequencing coverage, an effort that is heretofore also unattainable with single-cell gene expression workflows. Further, diseases that result from underlying genetic disorders require the ability to faithfully reconstruct genomic composition for both diagnosis and uncovering etiology. In particular, characterizing somatic mosaicism, which is the result of post-zygotic mutations and known to contribute to severe neurological disorders, necessitates the sampling of a large number of individual cells—a task far from tractable with current methods. The inability of previously described approaches to resolve these critical features has highlighted a profound deficit in the field's ability to faithfully characterize complex biological systems. These limitations emanate from the inability of known approaches to efficiently capture long-range DNA information with current sequencing technologies. Accordingly, a need exists for approaches capable of optimizing capture of long-range DNA information on current long-read sequencing platforms.

BRIEF SUMMARY OF THE INVENTION

The current disclosure relates, at least in part, to compositions and methods for performing nucleic acid sequencing, particularly upon chimeric nucleic acids using long-read sequencing platforms. In certain aspects, the instant disclosure provides methods and compositions for high-throughput construction and use of chimeric arrays of nucleic acids (via a process herein termed "Chimeric Array Sequencing", or "CAseq"), for application to long-read sequencing platforms. Such chimeric arrays allow for resolution of previously obscured genetic features, including detection of alternative splicing; improved detection of clonal evolution, including tumor clonal evolution; faithful reconstruction of genomic composition, e.g., for disease diagnosis and uncovering disease etiology; characterizing somatic mosaicism; and enhanced genomic haplotype assessment more generally; among others.

The current disclosure takes advantage of the unique characteristics of long-read platforms to provide a generalizable workflow for boosting output of multiple common sequencing libraries. While long read sequencers have a very large sequencing output (e.g., PacBio® Sequel II is ~300 GB) they are limited in the total number of reads per run (e.g., PacBio® Sequel II is ~4M). To maximize output, libraries of smaller fragments can be assembled into arrays and efficiently sequenced on long-read sequencers, boosting the number of sequenced library members linearly with respect to the number of fragments in the array. Certain aspects of the instant disclosure therefore detail a streamlined and generalizable method for assembly of arrays for high efficiency long-read sequencing, with a primary benefit of the instant disclosure that of enabling high throughput full-transcript sequencing from single-cell gene expression samples.

In one aspect, the instant disclosure provides a method for preparing an array nucleic acid sequence, the method involving: (i) obtaining a plurality of input nucleic acid sequences, where each of the input sequences is of approximately 300 kilobases in length or shorter (optionally 30 kilobases in length or shorter); (ii) attaching one or more adapter sequences to the plurality of nucleic acid sequences, thereby generating a population of adapted nucleic acid sequences; (iii) contacting the population of adapted nucleic acid sequences with an enzyme capable of generating single-stranded ends on at least one end of each double-stranded adapted nucleic acid sequence within the population of adapted nucleic acid sequences, thereby forming a population of nucleic acid sequences having single-stranded ends; and (iv) contacting the population of nucleic acid sequences having single-stranded ends with a ligase, thereby forming an array nucleic acid sequence.

In some embodiments, at least one of the adapter sequences includes an internal dU on one strand.

In embodiments, the array nucleic acid sequence has a length of at least 20 kilobases. Optionally, the array nucleic acid sequence has a length of at least 50 kilobases. In a related embodiment, the array nucleic acid sequence has a length of approximately 100 kilobases or more.

In one embodiment, the plurality of input nucleic acid sequences is of approximately 0.5 kb-20 kb in length.

In certain embodiments, the plurality of input nucleic acid sequences is obtained from one or more cDNA libraries. Optionally, the plurality of input nucleic acid sequences is obtained from one or more single-cell or spatial cDNA libraries.

In embodiments, step (ii) includes contacting the plurality of nucleic acid sequences with paired amplification primers, where at least one of the paired amplification primers includes an adapter sequence involving an internal dU on one strand, and performing at least one round of amplification, thereby generating a population of adapted nucleic acid sequences.

In some embodiments, at least one of each pair of amplification primers is biotinylated. Optionally, a biotin-mediated selection for adapter sequence-tailed amplicons is performed.

In embodiments, step (iii) includes contacting the population of adapted nucleic acid sequences with Uracil DNA glycosylase and Endonuclease VIII, thereby forming a population of nucleic acid sequences having single-stranded ends.

In some embodiments, the adapter sequence includes from 5-30 base pairs in length (excluding target nucleic acid sequence). Optionally, the adapter sequence is 6-25 base pairs in length. Optionally, the adapter sequence has the structure 5'-N6-16_dU_target-DNA-3'.

In embodiments, the adapter sequence that has an internal dU on one strand includes a sequence of SEQ ID NOs: 1-18.

In some embodiments, for a plurality of nucleic acid sequences with an adapter sequence, each adapter sequence possesses one or two designated sequence(s) that are complementary with at least one other of the plurality of nucleic acid sequences with an adapter sequence, where the plurality of adapter sequences thereby forms a population of complementary adapter sequences. Optionally, each complementary adapter sequence of the population of complementary adapter sequences possesses minimal similarity to each other complementary adapter sequence of the population of complementary adapter sequences. In related embodiments, each complementary adapter sequence of the population of complementary adapter sequences is at least 11 hamming distance units apart from all other complementary adapter sequences of the population of complementary adapter sequences.

In certain embodiments, one or more of the following is size-selected: the plurality of input nucleic acid sequences; the population of adapted nucleic acid sequences; and/or the population of nucleic acid sequences having single-stranded ends. Optionally, the size-selection is performed via electrophoresis. In a related embodiment, the size-selection is performed using an agarose gel.

In certain embodiments, sequence information of the array nucleic acid sequence is obtained. Optionally, the sequence information of the array nucleic acid sequence is obtained using a long-read sequencing platform.

In related embodiments, haplotype-phased sequence information is obtained across the array nucleic acid sequence.

In another embodiment, the array nucleic acid sequence that is formed includes five or more input nucleic acid sequences. Optionally, the array nucleic acid sequence that is formed includes six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more input nucleic acid sequences.

In certain embodiments, targeted isoform sequencing information is obtained via targeting of gene panels during step (i) obtaining the plurality of input nucleic acid sequences.

In embodiments, the plurality of input nucleic acid sequences includes cDNAs for immune response pathways.

In some embodiments, the plurality of input nucleic acid sequences is obtained from mitochondrial DNA. Optionally, sequencing of the array nucleic acid sequence is used for mitochondrial DNA lineage tracing.

In certain embodiments, the population of adapted nucleic acid sequences is joined via Gibson assembly.

In some embodiments, the array nucleic acid sequence is a linear array.

In certain embodiments, the array nucleic acid sequence is a circular array.

An additional aspect of the instant disclosure provides a method for obtaining isoform sequencing information from a population of input cDNA sequences, the method involving: (i) obtaining a plurality of input cDNA sequences; (ii) contacting the plurality of cDNA sequences with paired amplification primers, where at least one of the paired amplification primers presents an adapter sequence that includes an internal dU on one strand and performing at least one round of amplification, thereby generating a population of adapted cDNA sequences; (iii) contacting the population of adapted cDNA sequences with Uracil DNA glycosylase and Endonuclease VIII, thereby forming a population of adapted cDNA sequences having single-stranded ends; (iv) contacting the population of adapted cDNA sequences having single-stranded ends with a ligase, thereby forming a linear array nucleic acid sequence; (v) obtaining sequence information from the linear array nucleic acid sequence (optionally, the sequence is obtained via long-read sequencing); and (vi) analyzing the sequence information obtained from the linear array nucleic acid sequence to obtain isoform sequencing information, thereby obtaining isoform sequencing information from the population of input cDNA sequences.

Another aspect of the instant disclosure provides a method for performing mitochondrial lineage tracing from a population of input mitochondrial cDNA sequences, the method involving: (i) obtaining a plurality of input mitochondrial cDNA sequences; (ii) contacting the plurality of mitochondrial cDNA sequences with paired amplification primers, where at least one of said paired amplification primers that includes an adapter sequence comprising an internal dU on one strand and performing at least one round of amplification, thereby generating a population of adapted mitochondrial cDNA sequences; (iii) contacting the population of adapted mitochondrial cDNA sequences with Uracil DNA glycosylase and Endonuclease VIII, thereby forming a population of adapted mitochondrial cDNA sequences having single-stranded ends; (iv) contacting the population of adapted mitochondrial cDNA sequences having single-stranded ends with a ligase, thereby forming an array nucleic acid sequence; (v) obtaining sequence information from the array nucleic acid sequence (optionally, the sequence is obtained via long-read sequencing); and (vi) analyzing the sequence information obtained from the linear array nucleic acid sequence to trace mitochondrial lineage, thereby performing mitochondrial lineage tracing upon the population of input mitochondrial cDNA sequences. An additional aspect of the instant disclosure provides a method for preparing an array of linear arrays of nucleic acid sequence, the method involving: (i) preparing a first linear array from a first population of input nucleic acid sequences by the CAseq method disclosed herein; (ii) preparing a second linear array from a second population of input nucleic acid sequences by the CAseq method disclosed herein, where the first linear array and the second linear array each possesses a compatible complementary flanking sequence; (iii) combining the first linear array and the second linear array in solution; and (iv) contacting the first linear array and the second linear array in solution with a ligase, thereby forming an array of linear arrays of nucleic acid sequence.

In certain embodiments, the first linear array or the second linear array, or both, include an array of linear arrays.

In some embodiments, the method further involves (v) preparing a third linear array from a third population of input nucleic acid sequences by the CAseq method disclosed herein, where the array of linear arrays and the third linear array each possesses a compatible complementary flanking sequence; (vi) combining the array of linear arrays and the third linear array in solution; and (vii) contacting the array of linear arrays and the third linear array in solution with a ligase, thereby forming a larger array of linear arrays of nucleic acid sequence. Optionally, steps (v)-(vii) are repeated to incorporate a fourth linear array, a fifth linear array, and/or more linear arrays into the larger array of linear arrays.

Another aspect of the instant disclosure provides a method for preparing an array nucleic acid sequence, the method involving: (a) obtaining a plurality of input nucleic acid sequences, where each input sequence is of approximately 300 kilobases in length or shorter; (b) contacting the plurality of nucleic acid sequences with an adapter sequence that includes an internal dU on one strand and a ligase, thereby generating a population of adapted nucleic acid sequences; (c) contacting the population of adapted nucleic acid sequences with Uracil DNA glycosylase and Endonuclease VIII, thereby forming a population of nucleic acid sequences having single-stranded ends; and (d) contacting the population of nucleic acid sequences having single-stranded ends with a ligase, thereby forming an array nucleic acid sequence.

In an additional aspect, the instant disclosure provides a method for preparing an array nucleic acid sequence, the method involving: (i) obtaining a plurality of input nucleic acid sequences, where each input sequence is of approximately 300 kilobases in length or shorter; (ii) contacting the plurality of nucleic acid sequences with an adapter sequence having an internal dU on one strand and performing at least one round of amplification, thereby generating a population of adapted nucleic acid sequences; (iii) contacting the population of adapted nucleic acid sequences with Uracil DNA glycosylase and Endonuclease VIII, thereby forming a population of nucleic acid sequences having single-stranded ends; and (iv) contacting the population of nucleic acid sequences having single-stranded ends with a ligase, thereby forming a linear array nucleic acid sequence.

In embodiments, each input nucleic acid sequence within the plurality of input sequences is of approximately 30 kilobases in length or shorter.

A further aspect of the instant disclosure provides a composition that includes a plurality of nucleic acid sequences, where at least two of the plurality of nucleic acid sequences includes an adapter sequence selected from SEQ ID NOs: 1-18.

Another aspect of the instant disclosure provides a kit that includes a plurality of adapter sequences selected from SEQ ID NOs: 1-18, and instructions for its use.

A further aspect of the instant disclosure provides a method for identifying discrete sequence elements within individual nucleic acid sequence reads of a population of nucleic acid sequence reads, the individual nucleic acid sequence reads having a linear array of sequence elements, where each of the linear array of sequence elements includes two or more nucleic acid sequence elements drawn from a library of high complexity, where each nucleic acid sequence element drawn from a library of high complexity is flanked either by one or more expected nucleic acid sequences drawn from a library of low complexity or by one or more expected nucleic acid sequences drawn from a library of low complexity and a sequence read terminus, the method involving: (a) applying one or more statistical annotation models to sequence data of the population of nucleic acid sequence reads, to predict within the population of nucleic acid sequence reads regions of individual nucleic acid sequence elements drawn from a library of high complexity and regions of nucleic acid sequences drawn from a library of low complexity, where the one or more statistical annotation models include: i) a generative statistical alignment model for recognizing one or more expected nucleic acid sequences interspersed throughout a nucleic acid sequence read; and ii) a random statistical alignment model for recognizing sequences not known or drawn from a dictionary of sequences of high complexity, where predicted transition sites are placed at the termini of each model and disallowed within internal positions in the generative statistical alignment model; (b) repeating step (a) upon a plurality of nucleic acid sequence reads, thereby applying the one or more statistical models to each nucleic acid sequence read of the plurality of nucleic acid sequence reads in both forward and reverse-complement orientations, and determining a maximum a posteriori state path Final per-read model selection chosen by identifying the model with the greatest log likelihood value; and (c) segmenting each nucleic acid sequence read of the plurality of nucleic acid sequence reads into discrete sequence elements partitioned by transition sites identified by the maximum a posteriori state path Final per-read model selection of step (b), thereby identifying discrete sequence elements within the population of nucleic acid sequence reads.

In one embodiment, the library of high complexity includes or potentially includes more than 1,000 different elements. Optionally, the library of high complexity includes or potentially includes more than 10,000 different elements.

In another embodiment, the library of high complexity and/or the sequences not known a priori or that are drawn from a dictionary of sequences of high complexity include elements that are cDNA transcript sequences, barcode sequences, and/or unique molecular identifiers.

In certain embodiments, the library of low complexity includes 100 or fewer different sequences. Optionally, the library of low complexity includes 50 or fewer different sequences. Optionally, the library of low complexity includes 25 or fewer different sequences. Optionally, the library of low complexity includes 15 or fewer different sequences.

In some embodiments, the library of low complexity includes adapter and/or linker sequences.

In embodiments, the a priori expected nucleic acid sequences include adapter and/or linker sequences.

In certain embodiments, the sequences not known a priori or drawn from a dictionary of sequences of high complexity include one or more of the following types of sequences: cDNA sequences, barcode sequences and/or unique molecular identifier sequences. Optionally, the barcode sequences include single cell barcode sequences.

Another aspect of the instant disclosure provides a system for identifying discrete sequence elements within individual sequence reads of a plurality of nucleic acid sequence reads and storing sequence element data, the system including: one or more network interfaces to communicate with a network; a processor coupled to the network interfaces and configured to execute one or more processes; and a non-transitory memory configured to store a process executable by the processor, the process when executed configured to: (a) obtain a plurality of nucleic acid sequence reads including individual nucleic acid sequence reads having a linear array of sequence elements, where each read having a linear array of sequence elements includes two or more individual nucleic acid sequence elements drawn from a library of high complexity, where each nucleic acid sequence element drawn from a library of high complexity is flanked either by one or more expected nucleic acid sequences of low complexity or by one or more expected nucleic acid sequence of low complexity and a sequence read terminus; (b) apply one or more statistical annotation models to sequence data of the plurality of nucleic acid sequence reads, to predict within nucleic acid sequence reads of the plurality regions of individual nucleic acid sequence elements drawn from a library of high complexity and regions of nucleic acid sequences drawn from a library of low complexity, where the one or more statistical annotation models include: i) a generative statistical alignment model for recognizing one or more expected nucleic acid sequences interspersed throughout a nucleic acid sequence read; and ii) a random statistical alignment model for recognizing sequences not known or drawn from a dictionary of sequences of high complexity, where predicted transition sites are placed at the termini of each model and disallowed within internal positions in the generative statistical alignment model; (c) repeat step (a) upon a plurality of nucleic acid sequence reads, thereby applying the one or more statistical models to each nucleic acid sequence read of the plurality of nucleic acid sequence reads in both forward and reverse-complement orientations, and determine a maximum a posteriori state path Final per-read model selection chosen by identifying the model with the greatest log likelihood value, thereby labeling known segments within the nucleic acid sequence read; and (d) segment each nucleic acid sequence read of the plurality of nucleic acid sequence reads into discrete sequence elements (of labeled known segments) partitioned by transition sites identified by the maximum a posteriori state path Final per-read model selection of step (c), thereby identifying discrete sequence elements within the plurality of nucleic acid sequence reads; and (e) store the discrete sequence elements identified within the plurality of nucleic acid sequence reads in a sequence element data file.

An additional aspect of the instant disclosure provides a system for identifying as low quality and removing individual sequence reads of a plurality of nucleic acid sequence reads and storing sequence data, the system including: one or more network interfaces to communicate with a network; a processor coupled to the network interfaces and configured to execute one or more processes; and a non-transitory memory configured to store a process executable by the processor, the process when executed configured to: i) perform steps (a)-(e) above upon individual sequence reads of a plurality of nucleic acid sequence reads and ii) identify and remove any reads having discrete sequence elements that do not occur in the order expected as per library preparation, where reads that begin after the first discrete sequence element but for which remaining discrete sequence elements are in order, as well as reads that end before the final expected discrete sequence element but for which prior sections are all in order, and a combination of these cases, are not removed; and iii) store the plurality of nucleic acid sequence reads with low quality reads removed, in a sequence data file.

In certain embodiments, the individual sequence reads that Circular Consensus Sequencing software has identified as of high quality are identified by this method as being of low quality.

Another aspect of the instant disclosure provides a system for identifying individual sequence reads as of sufficiently high quality for further analysis and adding individual sequence reads of a plurality of nucleic acid sequence reads to sequence data and storing sequence data, the system including: one or more network interfaces to communicate with a network; a processor coupled to the network interfaces and configured to execute one or more processes; and a non-transitory memory configured to store a process executable by the processor, the process when executed configured to: i) perform steps (a)-(e) above upon individual sequence reads of a plurality of nucleic acid sequence reads and identify any reads having discrete sequence elements in the order in which they are expected to appear as per library preparation, including reads that begin after the first expected discrete sequence element but for which remaining discrete sequence elements are in order, as well as reads that end before the final expected discrete sequence element but for which prior discrete sequence elements are in order, and any combination of these cases, as of sufficiently high quality for further analysis; and v) store the nucleic acid sequence reads identified as of sufficiently high quality for further analysis in a sequence data file.

In certain embodiments, the individual sequence reads that Circular Consensus Sequencing software has identified as of low quality are identified by this method as being of high quality.

A final aspect of the instant disclosure provides a system for approximating the quality of newly identified high and low quality reads and adding an estimated quality score to data and storing data, the system including: one or more network interfaces to communicate with a network; a processor coupled to the network interfaces and configured to execute one or more processes; and a non-transitory memory configured to store a process executable by the processor, the process when executed configured to: (i) for each discrete sequence element in each newly identified high or low quality read, compute an observed alignment score between nucleotides in a discrete sequence element and an expected sequence for the discrete sequence element, and compute a best possible alignment score between nucleotides in the discrete sequence element and the expected sequence for the discrete sequence element; (ii) optionally divide the alignment score computed in step (i) by the best possible alignment score to get a quality score for each section; and (iii) sum all observed alignment scores computed in step (i) to obtain an overall observed alignment score; sum all best possible alignment scores computed in step (i) to obtain an overall best possible alignment score; and calculate an estimated quality score for the nucleic acid sequence read by obtaining a ratio of the overall observed alignment score to the overall best possible alignment score; and (iv) store the estimated quality score for the nucleic acid sequence read in a data file.

In certain embodiments, the alignment score is computed in step (a) directly using dynamic programming algorithms or directly by computing the Levenshtein distance between the discrete sequence element and the expected sequence and subtracting that distance from the length of the expected sequence. Optionally, the dynamic programming algorithms include one or more of: Smith-Waterman (local) algorithms, Needleman-Wunsch (global) algorithms, or similar/equivalent alignment algorithms (e.g. Pair Hidden Markov Models).

In some embodiments, the best possible alignment score is obtained by computing the alignment score between the expected sequence and itself.

Definitions

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value.

In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Unless otherwise clear from context, all numerical values provided herein are modified by the term "about."

By "control" or "reference" is meant a standard of comparison. Methods to select and test control samples are within the ability of those in the art. Determination of statistical significance is within the ability of those skilled in the art, e.g., the number of standard deviations from the mean that constitute a positive result.

As used herein, the term "different", when used in reference to nucleic acids, means that the nucleic acids have nucleotide sequences that are not the same as each other. Two or more nucleic acids can have nucleotide sequences that are different along their entire length. Alternatively, two or more nucleic acids can have nucleotide sequences that are different along a substantial portion of their length. For example, two or more nucleic acids can have target nucleotide sequence portions that are different for the two or more molecules while also having a universal sequence portion that is the same on the two or more molecules.

As used herein, the term "each," when used in reference to a collection of items, is intended to identify an individual item in the collection but does not necessarily refer to every item in the collection. Exceptions can occur if explicit disclosure or context clearly dictates otherwise.

As used herein, single cell nucleic acid sequencing refers to methods for measuring the sequence of cellular or other types of nucleic acids in a sample and identifying the individual cell(s) and/or source(s) from which the cellular and/or sample nucleic acid(s) were obtained. Similarly, single cell RNA sequencing refers to methods for measuring the sequence of cellular RNA(s) (optionally, transcripts) and identifying the individual cell(s) from which the cellular RNA(s) were obtained.

As used herein, the term "amplicon," when used in reference to a nucleic acid, means the product of copying the nucleic acid, wherein the product has a nucleotide sequence that is the same as or complementary to at least a portion of the nucleotide sequence of the nucleic acid. An amplicon can be produced by any of a variety of amplification methods that use the nucleic acid, or an amplicon thereof, as a template including, for example, polymerase extension, polymerase chain reaction (PCR), rolling circle amplification (RCA), multiple displacement amplification (MDA), ligation extension, or ligation chain reaction. An amplicon can be a nucleic acid molecule having a single copy of a particular nucleotide sequence (e.g. a PCR product) or multiple copies of the nucleotide sequence (e.g. a concatameric product of RCA). A first amplicon of a target nucleic acid is typically a complementary copy. Subsequent amplicons are copies that are created, after generation of the first amplicon, from the target nucleic acid or from the first amplicon. A subsequent amplicon can have a sequence that is substantially complementary to the target nucleic acid or substantially identical to the target nucleic acid.

As used herein, the term "array" refers to a population of features or sites that can be differentiated from each other according to relative location. Different molecules that are at different sites of an array can be differentiated from each other according to the locations of the sites in the array. An individual site of an array can include one or more molecules of a particular type. For example, a site can include a single nucleic acid molecule having a particular sequence or a site can include several nucleic acid molecules. In certain embodiments, the term "linear array" is used to refer to a linear assemblage of arrayed sequence elements, at discrete positions along a larger linear nucleic acid molecule.

As used herein, the term "barcode sequence" is intended to mean a series of nucleotides in a nucleic acid that can be used to identify the nucleic acid, a characteristic of the nucleic acid (e.g., the identity), or a manipulation that has been carried out on the nucleic acid. The barcode sequence can be a naturally occurring sequence or a sequence that does not occur naturally in the organism from which the barcoded nucleic acid was obtained. A barcode sequence can be unique to a single nucleic acid species in a population or a barcode sequence can be shared by several different nucleic acid species in a population. By way of further example, each nucleic acid probe in a population can include different barcode sequences from all other nucleic acid probes in the population. Alternatively, each nucleic acid probe in a population can include different barcode sequences from some or most other nucleic acid probes in a population. For example, each probe in a population can have a barcode that is present for several different probes in the population even though the probes with the common barcode differ from each other at other sequence regions along their length. In particular embodiments, one or more barcode sequences that are used with a biological specimen (e.g., a tissue sample) are not present in the genome, transcriptome or other nucleic acids of the biological specimen. For example, barcode sequences can have less than 80%, 70%, 60%, 50% or 40% sequence identity to the nucleic acid sequences in a particular biological specimen.

As used herein, the term "extend," when used in reference to a nucleic acid, is intended to mean addition of at least one nucleotide or oligonucleotide to the nucleic acid. In particular embodiments, one or more nucleotides can be added to the 3' end of a nucleic acid, for example, via polymerase catalysis (e.g. DNA polymerase, RNA polymerase or reverse transcriptase). Chemical or enzymatic methods can be used to add one or more nucleotide to the 3' or 5' end of a nucleic acid. One or more oligonucleotides can be added to the 3' or 5' end of a nucleic acid, for example, via chemical or enzymatic (e.g. ligase catalysis) methods. A nucleic acid can be extended in a template directed manner, whereby the product of extension is complementary to a template nucleic acid that is hybridized to the nucleic acid that is extended.

As used herein, the term "reverse transcriptase" refers to an enzyme used to generate complementary DNA (cDNA) from an RNA template. Reverse transcriptases (RTs) commonly used in the art include the non-strand displacing transcriptase RTX, and the viral reverse transcriptase M-MLV.

As used herein, "amplify", "amplifying" or "amplification reaction" and their derivatives, refer generally to any action or process whereby at least a portion of a nucleic acid molecule is replicated or copied into at least one additional nucleic acid molecule. The additional nucleic acid molecule optionally includes sequence that is substantially identical or substantially complementary to at least some portion of the template nucleic acid molecule. The template nucleic acid molecule can be single-stranded or double-stranded and the additional nucleic acid molecule can independently be single-stranded or double-stranded. Amplification optionally includes linear or exponential replication of a nucleic acid molecule. In some embodiments, such amplification can be performed using isothermal conditions; in other embodiments, such amplification can include thermocycling. In some embodiments, the amplification is a multiplex amplification that includes the simultaneous amplification of a plurality of target sequences in a single amplification reaction. The amplification reaction can include any of the amplification processes known to one of ordinary skill in the art. In some embodiments, the amplification reaction includes polymerase chain reaction (PCR) amplifying one or more nucleic acid sequences. Such amplification can be linear or exponential. In some embodiments, the amplification conditions can include isothermal conditions or alternatively can include thermocycling conditions, or a combination of isothermal and thermocycling conditions. In some embodiments, the conditions suitable for amplifying one or more nucleic acid sequences include polymerase chain reaction (PCR) conditions. Typically, the amplification conditions refer to a reaction mixture that is sufficient to amplify nucleic acids such as one or more target sequences flanked by a universal sequence, or to amplify an amplified target sequence ligated to one or more adapters. Generally, the amplification conditions include a catalyst for amplification or for nucleic acid synthesis, for example a polymerase; a primer that possesses some degree of complementarity to the nucleic acid to be amplified; and nucleotides, such as deoxyribonucleotide triphosphates and ribononucleic triphosphates to promote extension of the primer once hybridized to the nucleic acid. The amplification conditions can require hybridization or annealing of a primer to a nucleic acid, extension of the primer and a denaturing step in which the extended primer is separated from the nucleic acid sequence undergoing amplification. As used herein, the term "polymerase chain reaction" ("PCR") refers to the method of Mullis U.S. Pat. Nos. 4,683,195 and 4,683,202, which describe a method for increasing the concentration of a segment of a polynucleotide of interest. As used herein, "amplified target sequences" and its derivatives, refers generally to a nucleic acid sequence produced by the amplifying the target sequences using target-specific primers and the methods provided herein. The amplified target sequences may be either of the same sense (i.e. the positive strand) or antisense (i.e., the negative strand) with respect to the target sequences.

As used herein, the term "Circular Consensus Sequencing software low quality read" refers to a sequencing read to which Circular Consensus Sequencing software assigns a read quality score of less than 0.99, or to a read for which Circular Consensus Sequencing software assigns the read to a category other than "ZMWs pass filters".

As used herein, the term "Circular Consensus Sequencing software high quality read" refers to a sequence read for which Circular Consensus Sequencing software assigns the read to the "ZMWs pass filters" category. In certain embodiments, a CCS software high quality read is a read to which CCS software has assigned a read quality score of 0.99 or greater.

As used herein, the term "library of high complexity" refers to a library that contains, or potentially contains, a sufficiently large number of distinct elements (elements having different sequences, sizes, lengths, etc.) to render a priori prediction of whether a particular library element is present at a given location statistically uncertain (e.g., <1% chance of a particular library element at a given location, <0.1% chance of a particular library element at a given location, etc.). In certain embodiments, a "library of high complexity" contains, or potentially contains, more than 100 distinct elements, optionally more than 1000 distinct elements, optionally more than 10,000 distinct elements, and/or optionally more than 100,000 distinct elements. In embodiments, a "library of high complexity" refers to a cDNA sequence library, optionally a genomic cDNA sequence library. In some embodiments, a "library of high complexity" refers to a library drawn from a dictionary of sequences so large as to merit different considerations at a later processing step (e.g., barcode sequences (optionally single cell barcode sequences, bead barcode sequences, etc.), unique molecular identifiers, etc.).

As used herein, the term "library of low complexity" refers to a library that contains, or potentially contains, a sufficiently small number of distinct elements (elements having different sequences, sizes, lengths, etc.) to render a priori prediction of whether a particular library element is present at a given location possible with only limited statistical uncertainty (e.g., >1% chance of a particular library element occurring at a given location, >5% chance of a particular library element at a given location, >20% chance of a particular library element at a given location, etc.). In certain embodiments, a "library of low complexity" contains, or potentially contains, fewer than 100 distinct elements, optionally fewer than 50 distinct elements, optionally fewer than 30 distinct elements, and/or optionally fewer than 15 distinct elements. In embodiments, a "library of low complexity" refers to a linker and/or adapter sequence library.

As used herein, the terms "ligating", "ligation" and their derivatives refer generally to the process for covalently linking two or more molecules together, for example covalently linking two or more nucleic acid molecules to each other. In some embodiments, ligation includes joining nicks between adjacent nucleotides of nucleic acids. In some embodiments, ligation includes forming a covalent bond between an end of a first and an end of a second nucleic acid molecule. In some embodiments, the ligation can include forming a covalent bond between a 5' phosphate group of one nucleic acid and a 3' hydroxyl group of a second nucleic acid thereby forming a ligated nucleic acid molecule. Generally, for the purposes of this disclosure, a library sequence (optionally an amplified library sequence) can be ligated to an adapter sequence (or otherwise attached via primer-mediated amplification) to generate an adapter-ligated sequence, which can then be manipulated further to achieve joining of distinct sequence elements into a linear array nucleic acid.

As used herein, "ligase" and its derivatives, refers generally to any agent capable of catalyzing the ligation of two substrate molecules. In some embodiments, the ligase includes an enzyme capable of catalyzing the joining of nicks between adjacent nucleotides of a nucleic acid. In some embodiments, the ligase includes an enzyme capable of catalyzing the formation of a covalent bond between a 5' phosphate of one nucleic acid molecule to a 3' hydroxyl of another nucleic acid molecule thereby forming a ligated nucleic acid molecule. Suitable ligases may include, but are not limited to, T4 DNA ligase, T7 DNA ligase, Taq DNA ligase, and *E. coli* DNA ligase.

As used herein, "ligation conditions" and its derivatives, generally refers to conditions suitable for ligating two molecules to each other.

As used herein, the term "next-generation sequencing" or "NGS" can refer to sequencing technologies that have the capacity to sequence polynucleotides at speeds that were unprecedented using conventional sequencing methods (e.g., standard Sanger or Maxam-Gilbert sequencing methods). These unprecedented speeds are achieved by performing and reading out thousands to millions of sequencing reactions in parallel. NGS sequencing platforms include, but are not limited to, the following: Massively Parallel Signature Sequencing (Lynx Therapeutics); 454 pyro-sequencing (454 Life Sciences/Roche Diagnostics); solid-phase, reversible dye-terminator sequencing (Solexa/Illumina™); SOLiD™ technology (Applied Biosystems); Ion semiconductor sequencing (Ion Torrent™); and DNA nanoball sequencing (Complete Genomics). Descriptions of certain NGS platforms can be found in the following: Shendure, et al., "Next-generation DNA sequencing," Nature, 2008, vol. 26, No. 10, 135-1 145; Mardis, "The impact of next-generation sequencing technology on genetics," Trends in Genetics, 2007, vol. 24, No. 3, pp. 133-141; Su, et al., "Next-generation sequencing and its applications in molecular diagnostics" Expert Rev Mol Diagn, 2011, 11 (3):333-43; and Zhang et al., "The impact of next-generation sequencing on genomics", J Genet Genomics, 201, 38(3): 95-109.

As used herein, the terms "nucleic acid" and "nucleotide" are intended to be consistent with their use in the art and to include naturally occurring species or functional analogs thereof. Particularly useful functional analogs of nucleic acids are capable of hybridizing to a nucleic acid in a sequence specific fashion or capable of being used as a template for replication of a particular nucleotide sequence.

Naturally occurring nucleic acids generally have a backbone containing phosphodiester bonds. An analog structure can have an alternate backbone linkage including any of a variety of those known in the art. Naturally occurring nucleic acids generally have a deoxyribose sugar (e.g. found in deoxyribonucleic acid (DNA)) or a ribose sugar (e.g. found in ribonucleic acid (RNA)). A nucleic acid can contain nucleotides having any of a variety of analogs of these sugar moieties that are known in the art. A nucleic acid can include native or non-native nucleotides. In this regard, a native deoxyribonucleic acid can have one or more bases selected from the group consisting of adenine, thymine, cytosine or guanine and a ribonucleic acid can have one or more bases selected from the group consisting of uracil, adenine, cytosine or guanine. Useful non-native bases that can be included in a nucleic acid or nucleotide are known in the art. The terms "probe" or "target," when used in reference to a nucleic acid or sequence of a nucleic acid, are intended as semantic identifiers for the nucleic acid or sequence in the context of a method or composition set forth herein and does not necessarily limit the structure or function of the nucleic acid or sequence beyond what is otherwise explicitly indicated.

As used herein, the term "primer" and its derivatives refer generally to any nucleic acid that can hybridize to a target sequence of interest. Typically, the primer functions as a substrate onto which nucleotides can be polymerized by a polymerase or to which a nucleotide sequence such as an index can be ligated; in some embodiments, however, the primer can become incorporated into the synthesized nucleic acid strand and provide a site to which another primer can hybridize to prime synthesis of a new strand that is complementary to the synthesized nucleic acid molecule. The primer can include any combination of nucleotides or analogs thereof. In some embodiments, the primer is a single-stranded oligonucleotide or polynucleotide. The terms "polynucleotide" and "oligonucleotide" are used interchangeably herein to refer to a polymeric form of nucleotides of any length, and may include ribonucleotides, deoxyribonucleotides, analogs thereof, or mixtures thereof. The terms should be understood to include, as equivalents, analogs of either DNA, RNA, or cDNA and double stranded polynucleotides. The term as used herein also encompasses cDNA, that is complementary or copy DNA produced from a RNA template, for example by the action of reverse transcriptase. This term refers only to the primary structure of the molecule.

BRIEF DESCRIPTION OF THE DRAWINGS

The following detailed description, given by way of example, but not intended to limit the disclosure solely to the specific embodiments described, may best be understood in conjunction with the accompanying drawings, in which:

FIG. 1A shows a plot demonstrating that previously described sequencing approaches have left a gap in the isoform sequencing region. Specifically, there has been an absence of combined high-throughput (>20M reads) and intermediate-read length (0.5-5 kb) sequencing approaches, which the instant CAseq approach has been provided herein to address. FIG. 1R shows that the linear nucleic acid arrays disclosed herein can be sequenced on a long-read platform and demultiplexed into their individual full-length DNA fragments, multiplying the total output of sequenced DNA molecules equal to the number of fragments per array (3× as depicted in the current graphic, but 10-fold or greater multiplication of effective sequence output can be readily achieved). FIG. 1C shows a graphic depiction of how controlled and unbiased ligation of DNA amplicons into an array has been accomplished herein by a technique that employs deoxyuracil (dU) digestion to drive coordinated assembly of fragments. As exemplified, a DNA library is amplified with primers containing a 5' "complement sequence" followed by a dU. After amplification, the dU-containing amplicons are digested with Uracil DNA glycosylase and Endonuclease VIII, resulting in the removal of the dU and melting away of the remaining upstream strand of DNA, thereby exposing the single-stranded "complement sequence". These dU-digested amplicons can then hybridize with amplicons containing the complementary "complement sequence" to drive targeted assembly. Array length is simply modulated by the number of "overlap sequence" fragments that are generated.

FIGS. 2A and 2B show results obtained using the CAseq process of the instant disclosure, for an eight fragment multiplexed assembly from a cDNA library having an average fragment size of 1.2 kb. FIG. 2A shows that the CAseq process as so exemplified resulted in an ~10 kb multiplexed fragment upon ligation, per the cDNA size distributions displayed (starting, ligated and sequenced/demultiplexed cDNAs). FIG. 2B shows the results obtained for a multiplexed library sequenced on a Sequel II, which resulted in a total of ~2.5M reads, with ~23M transcripts after demultiplexing, which represented approximately a 9-fold increase in throughput over previously known approaches. Analysis of the demultiplexed reads confirmed a similar size distribution to the original cDNA library (as seen in FIG. 2A).

FIG. 3A shows distributions of count and length for protein coding gene transcripts (green dots, at left) and genes (black dots, distribution at right), across the human genome. While a vast majority of human protein coding gene transcripts are less than 10 kb in length, and effectively all protein coding transcripts are less than 100 kb in length, a significant majority of genes exceed 10 kb in length, with significant numbers of genes exceeding 100 kb in length and a number exceeding 1 Mb in length. FIG. 3B shows cumulative distributions (frequencies) in the human genome of protein coding gene transcript lengths (green dots, at left) and genes (black dots, distribution at right), represented in a manner that more clearly shows cumulative frequencies as lengths increase. 80% of human protein coding gene transcripts were specifically noted as containing fewer than 5000 bases.

Figure 5:
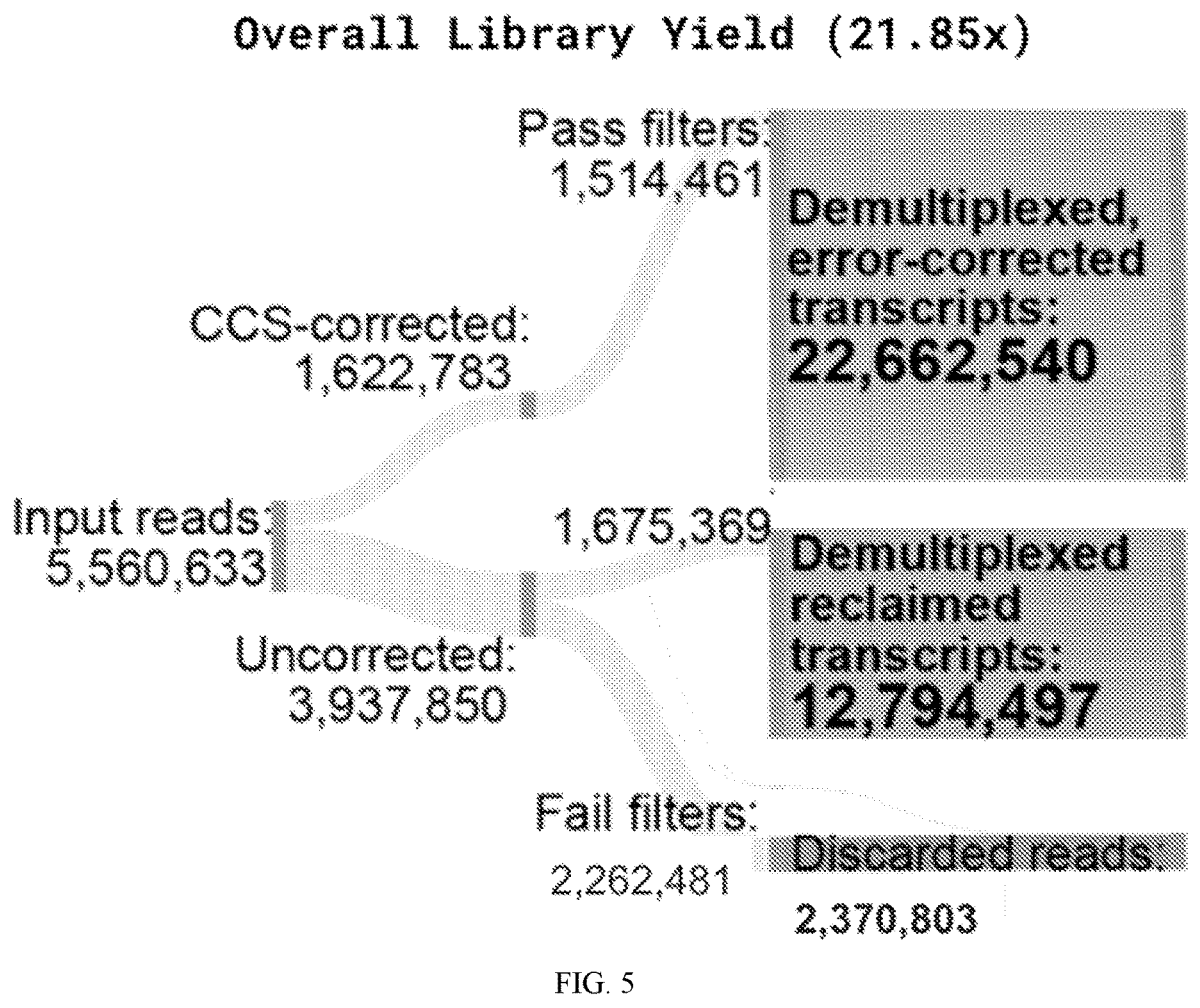

FIG. 5 shows a Sankey diagram of overall yield of the presently disclosed chimeric amplicon array sequencing method and analysis performed upon a human T-cell sample. The library preparation combined with the computational demultiplexing method and the low quality read reclamation method of the instant disclosure resulted in an overall 21.85× increase in data yield, as compared to methods using an extant CCS Corrected HiFi reads process (i.e. "Smart-seq3") alone.

FIG. 7 shows the top 20 ligation profiles (by prevalence) for a length 15 array library preparation with expected ligation order A->B->C->D->E->F->G->H->I->J->K->L->M->N->O->P. Reverse complemented adapters are indicated by the ' symbol. These data were not yet filtered by the analysis methods for chimeric arrays currently disclosed herein.

FIG. 8 shows a comparison between direct sequencing and using the presently disclosed chimeric amplicon array sequencing method and analysis, across two human T-cell samples.

FIG. 9A shows a heatmap of high-quality adapter ligations in a human T-cell sample prepared with the presently disclosed chimeric amplicon array sequencing method. Counts indicate the number of ligations from the overhang adapter indicated in each column to the overhang adapter indicated in each row. Reverse complemented sequences are indicated by the symbol. In this particular library, the array size was 15 and the expected ligation order was A->B->C->D->E->F->G->H->I->J->K->L->M->N->O->P. High quality data were determined by the presently disclosed chimeric amplicon array sequencing analysis process (termed "Longbow"). FIG. 9B shows a heatmap of low-quality adapter ligations in a human T-cell sample prepared with the presently disclosed chimeric amplicon array sequencing method. Counts indicate the number of ligations from the overhang adapter indicated in each column to the overhang adapter indicated in each row. Reverse complemented sequences are indicated by the ' symbol. In this particular library, the array size was 15 and the expected ligation order was A->B->C->D->E->F->G->H->I->J->K->L->M->N->O->P. Low quality data were determined by the presently disclosed chimeric amplicon array sequencing analysis process ("Longbow"). Though there are many ligations that do not occur on the diagonal, almost all ligations even in low-quality data occurred as expected.

FIG. 10A shows a t-SNE analysis plot clustered by phenotype. FIG. 10B shows a t-SNE analysis plot clustered by sample. FIG. 10C shows a plot of a t-SNE analysis performed using leiden clustering. FIG. 10D shows a t-SNE analysis plot clustered by cell type.

FIG. 11A shows the result of clustering of standard short-read gene expression data from the PBMC sample, used to identify immune cell types. FIG. 11B shows integration of the gene (short-read) and isoform (long-read) expression data from the same samples. FIG. 11C shows that the integration of the gene (short-read) and isoform (long-read) expression data shown in FIG. 11B revealed cell type specific expression of canonical CD45 (PTPRC) isoforms.

DETAILED DESCRIPTION OF THE INVENTION

Figure 1A:
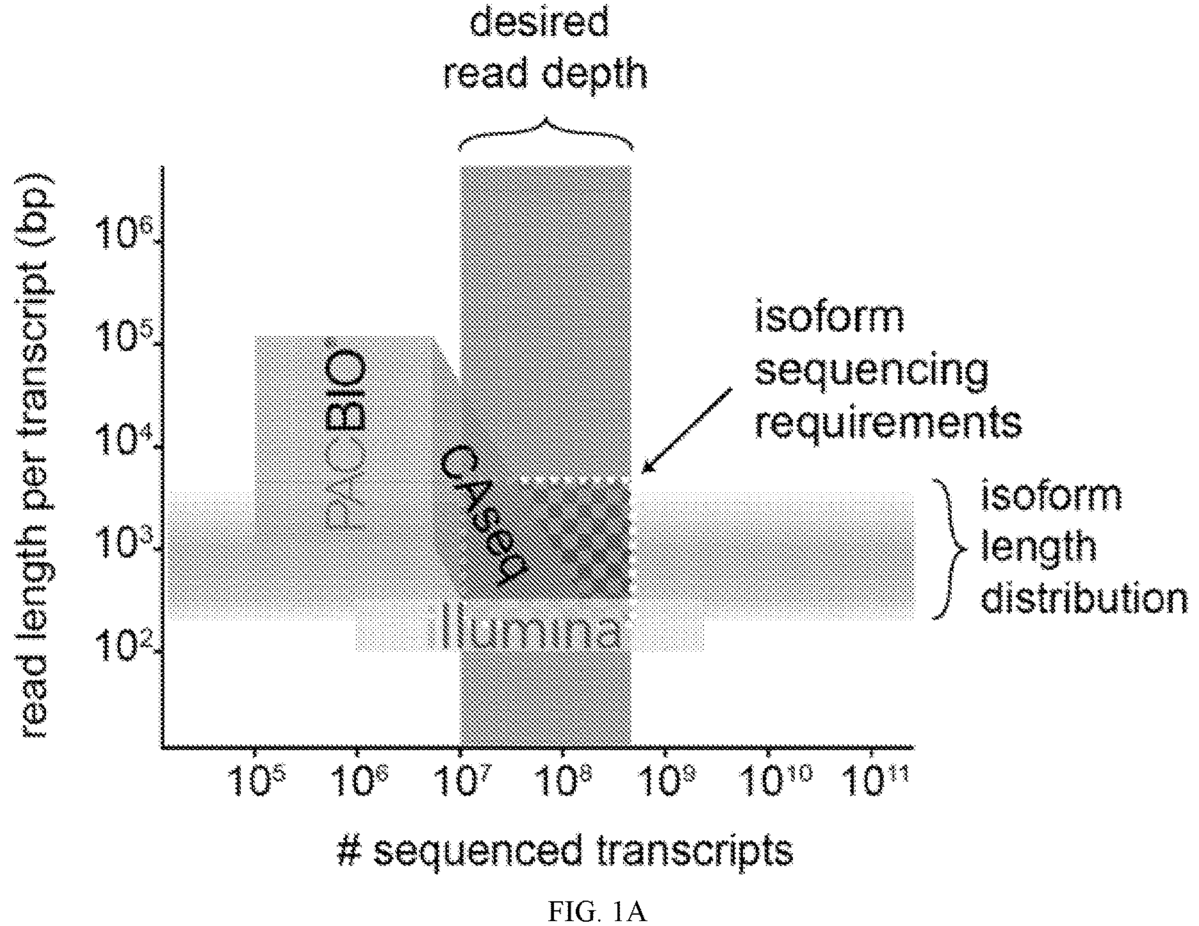
FIGS. 1A to 1C demonstrate the nucleic acid read length and throughput requirements for effective performance of isoform sequencing, and depict graphics presenting the "CAseq" approach disclosed herein.

The present disclosure is directed, at least in part, to methods and compositions for enhancing the throughput and/or yield of long-read sequencing platforms, in ways that are unbiased and/or that minimize any bias that might be found in input populations of nucleic acid sequences. Thus, in certain aspects, methods for performing nucleic acid sequencing, particularly upon chimeric nucleic acids using long-read sequencing platforms are provided. In certain embodiments, the linear chimeric arrays of nucleic acids of the instant methods are useful for application to long-read sequencing platforms. Such linear chimeric arrays allow for resolution of previously obscured genetic features, including detection of alternative splicing; improved detection of clonal evolution, including tumor clonal evolution; faithful reconstruction of genomic composition, e.g., for disease diagnosis and uncovering disease etiology; characterizing somatic mosaicism; and enhanced genomic haplotype assessment more generally; among others.

The current disclosure specifically takes advantage of the unique characteristics of long-read platforms to provide a generalizable workflow for boosting output of multiple common sequencing libraries. While long read sequencers have a very large sequencing output (e.g., PacBio® Sequel II is ~300 GB) they are limited in the total number of reads per run (e.g., PacBio® Sequel II is ~4M). To maximize output, libraries of smaller fragments can be assembled into arrays and efficiently sequenced on long-read sequencers, boosting the number of sequenced library members linearly with respect to the number of fragments in the array. Certain aspects of the instant disclosure therefore detail a streamlined and generalizable method for assembly of arrays for high efficiency long-read sequencing, with a primary benefit of the instant disclosure that of enabling high throughput full-transcript sequencing from single-cell gene expression samples.

Recent years have witnessed a dramatic increase in single-cell gene expression studies, yet a notable shortcoming of such studies has heretofore been an inability to resolve isoform composition or genetic variation in such efforts. Limitations in capturing full-length transcript information in high-throughput single-cell sequencing/expression analyses reflect a reliance upon high-throughput short-read sequencing in these workflows Short-read approaches effectively sequence small ~100 bp snapshots from the 5' or 3' end of the transcript, enough to efficiently acquire gene counts from $>1\times10^8$ transcripts, but too short to capture gene isoform composition or genetic variation (which would require read lengths of ~5 kb or more). While there have been impressive recent advancements in long-read sequencing technologies, their throughput remains insufficient to adequately sample full-length transcripts from single-cell gene expression samples. In certain aspects, provided herein is therefore a streamlined method to overcome these limitations, which in certain aspects relies upon creating precisely designed linear arrays of nucleic acid sequences for long-read sequencing platforms, with the instant method thereby enabling high throughput full-transcript sequencing from single-cell gene expression samples.

As noted above, significant recent advances in the two pioneering long-read sequencing platforms, produced by PacBio® and Oxford Nanopore Technologies ("Nanopore"), have dramatically increased the read length, throughput, and accuracy of long-read sequencing, placing the goal of single-cell isoform sequencing almost within reach. While recent efforts have leveraged the two long-read sequencing platforms (1-3), their workflows suffer from significant limitations related to high abundance of artifacts and lack of throughput. The sum of these inefficiencies has resulted in sparse sampling of transcriptomic content, which has to date severely constrained the power of long-read sequencing analyses. For example, R2C2 (Rolling Circle Amplification to Concatemeric Consensus), a Nanopore isoform sequencing method, has been observed to achieve only 52% of transcripts passing filter, equating to ~300,000 sequenced transcripts per Nanopore flowcell (~$790)(2). A PacBio® method, ScISOr-seq, has been similarly limited by artifacts, with only ~36% of reads passing filter, to ~360,000 full-length transcripts per PacBio® 1M flowcell (~$640)(1). These shortfalls have highlighted a gap that has heretofore been present between known sequencing technologies (FIG. 1A), specifically an absence of high-throughput (>20M reads) and intermediate-read length (0.5-5 kb) sequencing. Certain aspects of the instant disclosure provide a method, Chimeric Array Sequencing (CAseq), capable of increasing throughput of long-read sequencing platforms by >10× while also decreasing sequencing artifacts by >90% (FIG. 1A).

The CAseq method disclosed herein is a specialized multiplexing workflow that boosts molecular sequencing output of long-read sequencers by catering to the unique characteristics of these platforms. In contrast to Illumina®'s short-read sequencing workflows, which have specified read lengths, long-read platforms have indeterminate read lengths that can range from ~20 kb up to a staggering 2 Mb per pore (MinION, Oxford Nanopore Technologies) or well (Sequel II, PacBio®) in a flowcell. These massive read lengths are optimal for efforts such as bulk whole genome sequencing, but excessive for intermediate length targets (500 bp-10 kb) such as full-length transcripts.

Figure 1B:
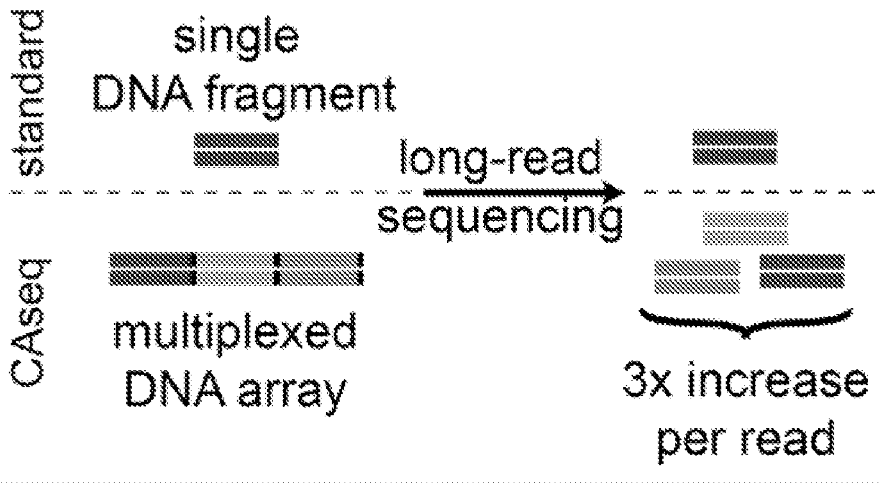
Figure 1C:
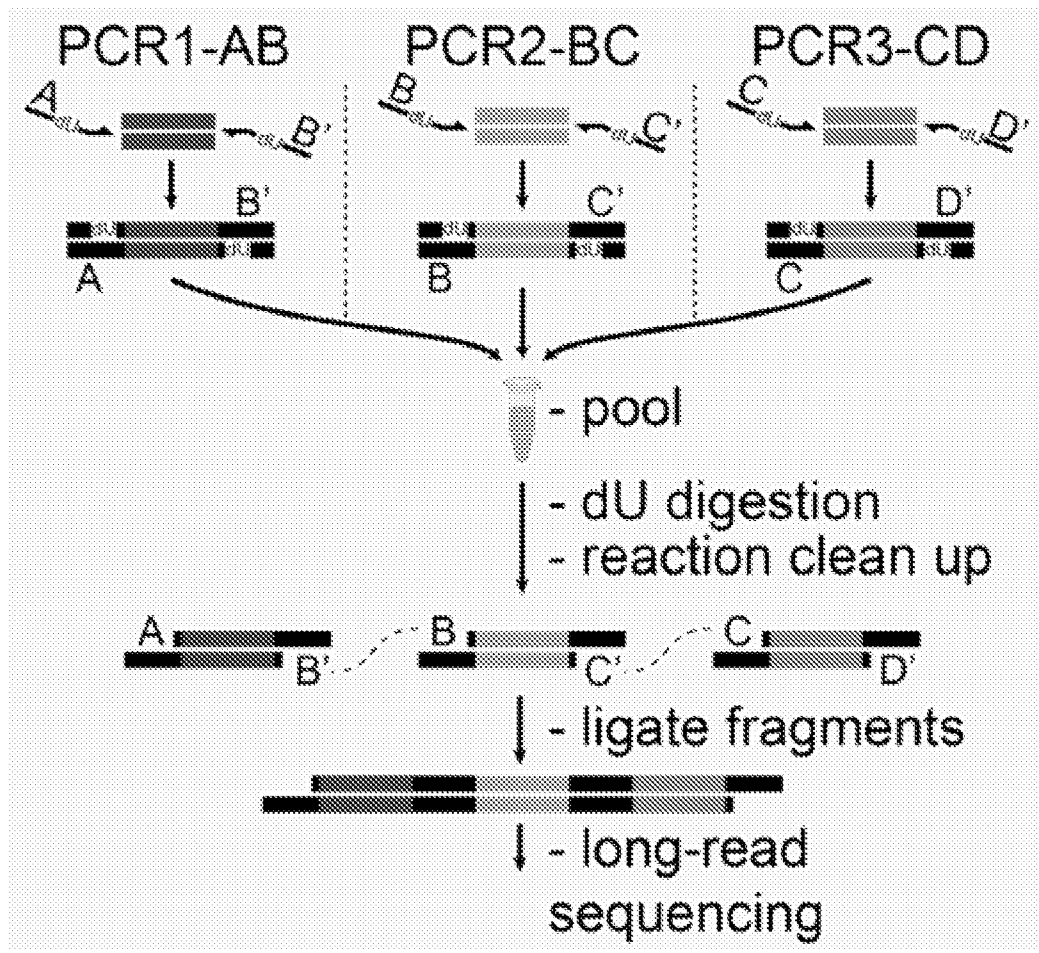

Chimeric Array Sequencing (CAseq), which enables the sequencing of multiple DNA targets from individual long-reads (FIG. 1A), has been developed herein to better adapt long-read sequencing platforms for scalable capture of intermediate-length targets. In the instant CAseq method, multiplexing of DNA fragments occurs via a controlled process of programmed ligation of a predetermined number of fragments into multi-fragment arrays. The linear nucleic acid arrays disclosed herein can be sequenced on a long-read platform and demultiplexed into their individual full-length DNA fragments, multiplying the total output of sequenced DNA molecules equal to the number of fragments per array (FIG. 1B). Controlled and unbiased ligation of DNA amplicons into an array is accomplished herein by a technique that employs deoxyuracil (dU) digestion to drive coordinated assembly of fragments. Briefly, a DNA library is amplified with primers containing a 5' "complement sequence" followed by a dU. After amplification, the dU-containing amplicons are digested with Uracil DNA glycosylase and Endonuclease VIII, resulting in the removal of the dU and melting away of the remaining upstream strand of DNA, thereby exposing the single-stranded "complement sequence". These dU-digested amplicons can then hybridize with amplicons containing the complementary "complement sequence" to drive targeted assembly. Array length is simply modulated by the number of "overlap sequence" fragments that are generated (FIG. 1C). Once assembled, these multiplexed fragments can enter standard Nanopore or PacBio® library prep workflows for subsequent sequencing. To generate very long or molecularly dense arrays, arrays can also be programmed to be ligated to one another, making arrays of arrays. In particular, it is expressly contemplated that to generate very large or dense multiplexed arrays with minimal sets of complementary sequences, arrays can, themselves, be ligated into arrays. In practice, this can be accomplished by first generating a number of primary arrays with a common core set of internal complementary sequences. The flanking fragments of these primary arrays can therefore be designed to contain unique complementary sequences that drive programmed ligation amongst the primary arrays (similar to the initial formation of the primary arrays).

It is expressly contemplated that the CAseq process disclosed herein can also be used in combination with any number of art-recognized technologies, including, but not limited to: (1) single-cell gene expression workflows, such as those of 10× Genomics®, e.g., processes in which barcoded populations of expressed nucleic acids can be constructed and optionally partitioned in gel beads (see, e.g., PCT/US2018/16019); (2) spatial sequencing workflows, such as the 10× Genomics® Visium spatial genomics process (Visium Spatial Gene Expression, which uses spatially barcoded mRNA-binding oligonucleotides grouped in spots within capture areas on specialized tissue slides; when mRNA is released from processed tissue sections, it binds to capture oligos in the vicinity; a cDNA library that incorporates these spatial barcodes and preserves spatial information can then be prepared from this mRNA; this gene expression data is subsequently layered over a high-resolution microscope image of the tissue section, making it possible to visualize what genes are expressed and where throughout the tissue sample.) and the "Slide-Seq" spatial transcriptome profiling approach disclosed within, e.g., US 2021/0123040; (3) mitochondrial lineage tracing can be performed from single-cell gene expression workflows using CAseq, by targeted amplification of mitochondrial genes, e.g., from 10× Genomics® samples; and (4) CAseq can be combined with high efficiency natively paired long-read sequencing of B-cell receptors (BCRs) and T-cell receptors (TCRs), among others.

In certain aspects, the instantly disclosed CAseq methods provide the ability to controllably and efficiently ligate DNA fragments into an array of defined fragment number, without sequence or library bias. In embodiments, the instant approaches modify ends of target DNA with defined sequences (e.g., of 6-16 bp in length, though other sequence lengths are also contemplated as viable, e.g., 5-25 bp or more in length) that possess an internal dU on one strand (e.g., 5'-N6-16_dU_target-DNA-3'). The end of the sequence is made single-stranded by base excision of the dU with Uracil DNA glycosylase (UDG) and the DNA glycosylase-lyase Endonuclease VIII (a USER enzyme cocktail from NEB®), which reveals the defined sequence for hybridization. Multiple families of these fragments can be made and processed to direct hybridization and subsequent ligation. Long arrayed fragments can then be sequenced on long-read platforms, thereby increasing their output of sequenced molecules. While the current complementary sequence mediated methods for preparing an arrayed sequence are exemplified herein, it is expressly contemplated that other routes for generating arrays could also be employed to make linear chimeric arrays, such as Gibson assembly, overlap extension (e.g., gene SOE), etc. For such applications, amplified fragments containing complementary end sequences to respective reactions are incubated and optionally cycled at appropriate conditions, thereby creating a chimeric array. It is also noted that one previously disclosed approach to creating long-read nucleic acid sequences employed restriction enzymes for assembly of chimeric sequences; however, the restriction endonuclease-mediated approach exhibited significant limitations in retaining library diversity ("SMURF-seq" of Prabakar et al., *Genome Biology* 20: 134)—limitations that the current CAseq processes overcome.

The currently disclosed CAseq processes have broad applicability across the field of sequencing. For genome sequencing, read length is important, as longer read lengths make sequence reconstruction easier and more accurate. The ability to amplify 0.5-20 kb fragments from the genome, then generate an amplicon array for high-efficiency long read sequencing increases the accuracy and fidelity of genome reconstruction and phasing. CAseq is also useful for whole exome and other target capture sequencing methods, as the approach enables phasing of SNPs from longer regions of DNA. Additionally, this CAseq is applicable to RNA sequencing of isoforms, as described in additional detail elsewhere herein. Short read sequencers are poorly suited to capture the RNA isoforms from traditional RNAseq workflows. Recent long-read efforts are low throughput and thus underpowered. The CAseq process of the instant disclosure increases the output of long-read sequencing significantly, thereby making CAseq a viable approach for understanding the isoform composition in a sample—notably isoform scRNAseq. The CAseq process of the instant disclosure is also contemplated as useful for natively paired sequencing of TCRα:TCRβ and $V_H$:$V_L$ pairs and amenable to integration of antigen-specific tags. E.g., the CAseq processes of the instant disclosure can be applied to extant processes for high throughput natively paired sequencing of TCR and Ig repertoires and library assemblies for whole genome and exome sequencing. Specifically, the CAseq process of the instant disclosure is provided as a long-read sequencing alternative to current workflows as noted in Tanno et al. (Science Advances. 6(17): eaay9093; DOI: 10.1126/sciadv.aay9093). Tanno et al. describes a method in which natively paired sequencing is achieved via an emulsion-based overlap extension RT-PCR performed upon the TCRα:TCRβ or $V_H$:$V_L$ pairs, thereby stitching them into one natively paired fragment. It is specifically contemplated herein, e.g., that pools of such paired amplicons can be used as input sequences in the CAseq workflow, thereby enabling scalable long-read sequencing of such pairs. Additionally, it is contemplated that other fragments can be integrated into the overlap extension RT-PCR during design of such chimeric arrays, thereby pairing more information from individual cells with such TCRα:TCRβ and/or $V_H$:$V_L$ pairs, rendering long-read sequencing essential for capture of all sequence information from such arrays.

In certain embodiments, the CAseq process of the instant disclosure is adapted to maximize upstream processing for generating DNA molecules to be assembled into an array. Examples include optimization of manners of fragmenting and amplifying DNA to generate larger size fragments (0.5-20 kb) with appropriate adapters, baiting of particular sequences from a fragmented DNA, and/or targeted amplification from DNA or RNA to enable targeted long read sequencing. Targeting DNA or RNA is contemplated as especially advantageous, as panels of target nucleic acids can be use to direct sequencing efforts: e.g., targeting can be employed to pay special attention to phasing of particular regions of the genome, to resolve complex/repetitive features of the genome, for targeted isoform amplification, and/or for tumor mitochondrial lineage tracing from single-cell gene expression/epigenome (ATAC)/genome samples, as also discussed elsewhere herein.

Various expressly contemplated components of certain methods and compositions of the instant disclosure are considered in additional detail below.

Nucleic Acid Libraries

The CAseq process of the instant disclosure can be applied to effectively any nucleic acid library, including RNA, cDNA and genomic DNA libraries. RNAs that can be detected and arrayed via the instant CAseq methods include mRNAs, snRNAs, lncRNAs, siRNAs, and gRNAs, with the current approach optionally employing/producing stabilized forms of such RNAs and/or corresponding DNA sequences for array and sequencing via the CAseq process.

Primers/Adapters

In exemplified aspects of the instant CAseq process, tailed primers are used to attach adapter sequences to an input nucleic acid population(s). The adapter sequences employed ultimately allow for chimeric array ligation to proceed via annealing of single-stranded "sticky ends" of individual input nucleic acid sequences, each with one or two adapter sequences attached at the end(s), to one another. Optionally, the design of complementary single-stranded sequences within the adapter sequences can be performed such that each chimeric array carries a precise linear order, or usage of the adapter sequences may allow for greater flexibility of linear ordering within each chimeric array. For certain exemplified embodiments, a family of dU-containing primers has been designed, for amplifying and appending 15 base pair (bp) complementary sequences to a full-length cDNA library, for multiplex ligation. To address a major source of artifactual sequences, the exemplified process has used biotinylated primers, to enable purification of full-length cDNA amplicons. To drive efficient multiplexing assembly and mitigate improper ligation events, the 15 bp complementary sequences as exemplified herein were designed to have minimal similarity by ensuring that all sequences be at least 11 hamming distance units apart from one another. An exemplary table of adapter sequences having such qualities if presented in Table 1 below.

TABLE 1

Exemplary List of Adapter Sequences Employed

| SEQ ID NO. | Complementary Sequences |
|---|---|
| 1 | AGCACCATAATGTGT |
| 2 | CTTGTAAGCTGTCTA |
| 3 | CTCTGTCAGGTCCGA |
| 4 | CCTCCTCCTCCAGAA |
| 5 | TCGCTGGTATTCCAA |
| 6 | GCTTACTTGTGAAGA |
| 7 | TAACCGTATGGTTGA |
| 8 | GATGGCGCTATCTCA |
| 9 | CTACCAGTGAGGAAG |
| 10 | GAGTCCAATTCGCAG |
| 11 | ATCAAGGCTTAACGG |
| 12 | TGTTGAATCCTAGCG |
| 13 | GTGCGTTGCGAATTG |
| 14 | CGGTAATGTACCGGC |
| 15 | ATTGCGTAGTTGGCC |
| 16 | CACTTGGTCGCAATC |
| 17 | GTAAGCCTTCGTGTC |
| 18 | CCTAGATCAGAGCCT |

While addition of adapter sequences to input sequences in the CAseq process has been exemplified herein using tailed amplification primers, it is expressly contemplated that other art-recognized methods for attaching adapter sequences to a population of input sequences can also be used. For example, particularly where it is advantageous to avoid amplifying fragments (e.g., due to length or maintaining modifications), direct ligation of adapters to input sequences (e.g., to blunt-ended input sequences) can be performed, prior to implementation of the remainder of the CAseq process disclosed herein for construction of linear arrays.

Lengths of Input Nucleic Acids (e.g., cDNAs)

Lengths of input nucleic acid sequences can range widely in size, depending upon the specific application of the instant disclosure. For cDNA populations as the input nucleic acids, lengths will commonly be distributed between 0.5 kb and 20 kb. However, it is expressly contemplated that the instant method can be applied to input nucleic acid sequence lengths as short as twenty nucleotides or less, or to input nucleic acid sequences/fragments possessing lengths of up to approximately a megabase or more in length. Indeed, it is expressly contemplated that the CAseq method of the instant disclosure can be applied to small <100 bp fragments, e.g., for capture from libraries, such as CITEseq tags or other biologically relevant information. As indicated above, the CAseq process of the instant disclosure can also be applied to standard size cDNAs of approximately 350 bp-10 kb. Further, as long-read sequencing lengths continue to increase, it is expressly contemplated that CAseq can be applied to make linear arrays of many large (>10 kb) nucleic acid sequences/fragments.

Uracil DNA Glycosylase

Certain aspects of the instant disclosure employ a Uracil DNA Glycosylase. Uracil-DNA glycosylase (UDG) is an enzyme that reverts mutations in DNA. The most common mutation is the deamination of cytosine to uracil. UDG repairs these mutations. UDG is crucial in DNA repair, without it these mutations may lead to cancer (Pearl, L H. *Mutat Res.* 460: 165-81).

Known uracil-DNA glycosylases and related DNA glycosylases (EC), include uracil-DNA glycosylase (Mol et al. *Cell.* 80: 869-78), thermophilic uracil-DNA glycosylase (Sandigursky and Franklin. *Curr. Biol.* 9: 531-4), G:T/U mismatch-specific DNA glycosylase (Mug) (Barrett et al. *Cell.* 92: 117-29), and single-strand selective monofunctional uracil-DNA glycosylase (SMUG1; Buckley and Ehrenfeld. *J. Biol. Chem.* 262: 13599-606).

Uracil DNA glycosylases remove uracil from DNA, which can arise either by spontaneous deamination of cytosine or by the misincorporation of dU opposite dA during DNA replication. The prototypical member of this family is *E. coli* UDG, which was among the first glycosylases discovered. Four different uracil-DNA glycosylase activities have been identified in mammalian cells, including UNG, SMUG1, TDG, and MBD4. They vary in substrate specificity and subcellular localization. SMUG1 prefers single-stranded DNA as substrate, but also removes U from double-stranded DNA. In addition to unmodified uracil, SMUG1 can excise 5-hydroxyuracil, 5-hydroxymethyluracil and 5-formyluracil bearing an oxidized group at ring C5 (Matsubara et al. *Nucleic Acids Res.* 32: 5291-5302). TDG and MBD4 are strictly specific for double-stranded DNA. TDG can remove thymine glycol when present opposite guanine, as well as derivatives of U with modifications at carbon 5. Current evidence suggests that, in human cells, TDG and SMUG1 are the major enzymes responsible for the repair of the U:G mispairs caused by spontaneous cytosine deamination, whereas uracil arising in DNA through dU misincorporation is mainly dealt with by UNG. MBD4 is thought to correct T:G mismatches that arise from deamination of 5-methylcytosine to thymine in CpG sites (Wu et al. *J. Biol. Chem.* 14: 5285-5291.). MBD4 mutant mice develop normally and do not show increased cancer susceptibility or reduced survival. But they acquire more C T mutations at CpG sequences in epithelial cells of the small intestine (Wong et al. *PNAS.* 99: 14937-14942). It is further contemplated that restriction enzymes can be used to prepare chimeric arrays (via annealing of complementary end sequences with other fragments). However, use of restriction enzymes in the CAseq process will very likely bias the library via digestion of certain fragments.

Endonuclease VIII

Certain exemplified aspects of the instant disclosure employ the Endonuclease VIII enzyme. Endonuclease VIII from *E. coli* acts as both an N-glycosylase and an AP-lyase. The N-glycosylase activity releases damaged pyrimidines from double-stranded DNA, generating an apurinic (AP site). The AP-lyase activity cleaves 3' and 5' to the AP site leaving a 5' phosphate and a 3' phosphate. Damaged bases recognized and removed by Endonuclease VIII include urea, 5, 6-dihydroxythymine, thymine glycol, 5-hydroxy-5-methylhydantoin, uracil glycol, 6-hydroxy-5, 6-dihydrothymine and methyltartronylurea. While Endonuclease VIII is similar to Endonuclease Endonuclease VIII has β and δ lyase activity while Endonuclease III has only β lyase activity.

Ligase

In certain aspects, once overhang ends of adapters have annealed to one another in the CAseq process, a ligase is administered, to fix chimeric array elements, attaching the elements in a linear series. A ligase generally refers to an enzyme that can catalyze the joining of two large molecules by forming a new chemical bond, usually with accompanying hydrolysis of a small pendant chemical group on one of the larger molecules or the enzyme catalyzing the linking together of two compounds, e.g., enzymes that catalyze joining of C—O, C—S, C—N, etc. In general, a ligase catalyzes the following reaction: Ab+C→A-C+b; or sometimes Ab+cD→A-D+b+c+d+e+f where the lowercase letters can signify the small, dependent groups. Ligase can join two complementary fragments of nucleic acid and repair single stranded breaks that arise in double stranded DNA during replication. Commonly used ligases include, without limitation, T4 DNA ligase, T7 DNA ligase, Taq DNA ligase, and *E. coli* DNA ligase, among others.

Long-Read Sequencing Platforms

Certain aspects of the instant disclosure employ, or involve preparation of nucleic acids that employ, long-read sequencing. Long-Read Sequencing (LRS) is a class of DNA sequencing methods currently under active development (Bleidorn, Christoph. *Systematics and Biodiversity* 14: 1-8). Long-read sequencing works by reading the nucleotide sequences at the single molecule level, in contrast to existing methods that require breaking long strands of DNA into small segments then inferring nucleotide sequences by amplification and synthesis ("Illumina sequencing technology" PDF).

NGS, as defined above, has dominated the DNA sequencing space since its development. It has dramatically reduced the cost of DNA sequencing by enabling a massively-paralleled approach capable of producing large numbers of reads at exceptionally high coverages throughout the genome (Treangen and Salzberg. *Nature Reviews Genetics* 13: 36-46).

NGS works by first amplifying the DNA molecule and then conducting sequencing by synthesis. The collective fluorescent signal resulting from synthesizing a large number of amplified identical DNA strands allows the inference of nucleotide identity. However, due to random errors, DNA synthesis between the amplified DNA strands would become progressively out-of-sync. Quickly, the signal quality deteriorates as the read-length grows. In order to preserve read quality, long DNA molecules must be broken up into small segments, resulting in a critical limitation of NGS technologies (Treangen and Salzberg). Computational efforts aimed to overcome this challenge often rely on approximative heuristics that may not result in accurate assemblies.

By enabling direct sequencing of single DNA molecules, long-read sequencing technologies have the capability to produce substantially longer reads than second generation sequencing (Bleidorn). Such an advantage has critical implications for both genome science and the study of biology in general. However, long-read sequencing data have much higher error rates than previous technologies, which can complicate downstream genome assembly and analysis of the resulting data (Gupta. *Trends in Biotechnology* 26: 602-611). These technologies are undergoing active development and it is expected that there will be improvements to the high error rates. For applications that are more tolerant to error rates, such as structural variant calling, long-read sequencing has been found to outperform existing methods.

Several companies are currently at the heart of long-read sequencing technology development, namely, Pacific Biosciences, Oxford Nanopore Technology, Quantapore (CA-USA), and Stratos (WA-USA). These companies are taking fundamentally different approaches to sequencing single DNA molecules.

PacBio® developed the sequencing platform of single molecule real time sequencing (SMRT), based on the properties of zero-mode waveguides. Signals are in the form of fluorescent light emission from each nucleotide incorporated by a DNA polymerase bound to the bottom of the zL well. A current example of a PacBio® long-read sequencing platform employed herein is ScISOr-seq.

Oxford Nanopore's technology involves passing a DNA molecule through a nanoscale pore structure and then measuring changes in electrical field surrounding the pore; while Quantapore has a different proprietary nanopore approach. Stratos Genomics spaces out the DNA bases with polymeric inserts, "Xpandomers", to circumvent the signal to noise challenge of nanopore ssDNA reading. R2C2 (Rolling Circle Amplification to Concatemeric Consensus) is noted as an exemplary Nanopore isoform sequencing method.

In certain embodiments, nanopore sequencing is employed (see, e.g., Astier et al., J. Am. Chem. Soc. 2006 Feb. 8; 128(5): 1705-10, which is incorporated by reference). The theory behind nanopore sequencing has to do with what occurs when a nanopore is immersed in a conducting fluid and a potential (voltage) is applied across it. Under these conditions a slight electric current due to conduction of ions through the nanopore can be observed, and the amount of current is exceedingly sensitive to the size of the nanopore. As each base of a nucleic acid passes through the nanopore (or as individual nucleotides pass through the nanopore in the case of exonuclease-based techniques), this causes a change in the magnitude of the current through the nanopore that is distinct for each of the four bases, thereby allowing the sequence of the DNA molecule to be determined.

While certain aspects of the instant disclosure employ specialized oligonucleotide primers designed to possess distinct complementary sequences that terminate at one or more dU residues and that can be used to prepare a linear tandem array of respective sequence elements, it is also contemplated that additional nucleic acid primers/sequences/adapters can also be added to the nucleic acid libraries of the instant disclosure. Such expressly contemplated additional primers/sequences/adapters include but are not limited to, e.g., sequence barcodes, such as those used in the CITE-Seq process (Stoeckius et al. Nature Methods. 14: 865-868), REAP-Seq process (Peterson et al. Nature Biotechnology. 35: 936-939), or in other processes; unique molecular identifiers (UMIs), such as those employed in Smith et at. (Smith, A. M. *Genuine Research* 19: 1836-1342) and elsewhere, among other identifier and/or adapter sequences. Such sequences can optionally added to library sequences at any time prior to the ligation step of the CAseq process, which fixes the order of the respective linear chimeric array sequence elements in advance of performance of long-read sequencing.

Barcode sequences and other identifying sequences can be any of a variety of lengths. Longer sequences, such as those prepared via the instant CAseq process, can generally accommodate a larger number and variety of barcodes for a population. Generally, plurality of individual elements in a chimeric array will have the same length barcode (albeit with different sequences), but it is also possible to use different length barcodes for different elements of a single array, or for different CAseq long-read sequences. A barcode sequence can be at least 2, 4, 6, 8, 10, 12, 15, 20 or more nucleotides in length. Alternatively or additionally, the length of the barcode sequence can be at most 20, 15, 12, 10, 8, 6, 4 or fewer nucleotides. Examples of barcode sequences that can be used are set forth, for example, in U.S. Patent Publication No. 2014/0342921 and U.S. Pat. No. 8,460,865, each of which is incorporated herein by reference.

It is contemplated that certain oligonucleotides of the instant disclosure can also include an additional linker (optionally a cleavable linker); a Unique Molecular Identifier (UMI) which differs for each priming site (as known in the art, e.g., see WO 2016/040476); a barcode sequence as described above; and optionally a common sequence ("PCR handle") to enable PCR amplification.

Single-Cell Sequencing/Molecular Profiling

Single-cell (SC) molecular profiling methods have already made major impacts on biomedical research as such methods have recently transitioned into the mainstream, doing so alongside pre-existing SC-sensitive approaches like FACS. Breakthroughs and rapid progress have made SC resolution at many "omics" (i.e. genomics, proteomics, transcriptomics, etc.) levels possible. Technical breakthroughs have driven performance and cost improvements of SC molecular profiling, and like next-generation sequencing (NGS) before it, SC analysis is now increasingly applied directly to patient care and pharmaceutical research.

Sequence Analysis and Systems

The instant disclosure encompasses not only chimeric amplicon arrays as identified herein but also computers and systems for implementing the provided methods.

General methods for obtaining samples, generating sequencing reads, and various types of sequencing useful for practicing the disclosure will now be described. It is to be understood that these exemplary methods are not limiting and may be modified as necessary by those skilled in the art.

Obtaining a plurality of sequence reads can include sequencing a nucleic acid from a sample to generate the sequence reads. Obtaining a plurality of sequence reads can also include receiving sequencing data from a sequencer. Nucleic acid in a sample can be any nucleic acid, including for example, genomic DNA in a tissue sample, cDNA amplified from a particular target in a laboratory sample, mixed DNA from multiple organisms, synthetic nucleic acid sequences (e.g., barcodes and unique molecular identifiers (UMIs)), etc. In one embodiment, nucleic acid template molecules (e.g., DNA or RNA) are isolated from a biological sample containing a variety of other components, such as proteins, lipids, and non-template nucleic acids. Nucleic acid template molecules can be obtained from any cellular material, obtained from animal, plant, bacterium, fungus, or any other cellular organism. Biological samples for use in the present disclosure also include viral particles or preparations. Nucleic acid template molecules can be obtained directly from an organism or from a biological sample obtained from an organism, e.g., from blood, urine, cerebrospinal fluid, seminal fluid, saliva, sputum, stool, and tissue. Any tissue or body fluid specimen (e.g., a human tissue of bodily fluid specimen) may be used as a source for nucleic acid to use in the disclosure. Nucleic acid template molecules can also be isolated from cultured cells, such as a primary cell culture or cell line. The cells or tissues from which template nucleic acids are obtained can be infected with a virus or other intracellular pathogen. A sample can also be total RNA extracted from a biological specimen, a cDNA library, viral, or genomic DNA. A sample may also be isolated DNA from a non-cellular origin, e.g. amplified/isolated DNA from the freezer.

Generally, nucleic acid can be extracted, isolated, amplified, or analyzed by a variety of techniques such as those described by Green and Sambrook, Molecular Cloning: A Laboratory Manual (Fourth Edition), Cold Spring Harbor Laboratory Press, Woodbury, N.Y. 2,028 pages (2012); or as described in U.S. Pat. Nos. 7,957,913; 7,776,616; 5,234,809; U.S. Pub. 2010/0285578; and U.S. Pub. 2002/0190663.

Nucleic acid obtained from biological samples may be fragmented to produce suitable fragments for analysis. Template nucleic acids may be fragmented or sheared to a desired length, using a variety of mechanical, chemical, and/or enzymatic methods. DNA may be randomly sheared via sonication using, for example, an ultrasonicator sold by Covaris (Woburn, Mass.), brief exposure to a DNase, or using a mixture of one or more restriction enzymes, or a transposase or nicking enzyme. RNA may be fragmented by brief exposure to an RNase, heat plus magnesium, or by shearing. The RNA may be converted to cDNA. If fragmentation is employed, the RNA may be converted to cDNA before or after fragmentation. In one embodiment, nucleic acid is fragmented by sonication. In another embodiment, nucleic acid is fragmented by a hydroshear instrument. Generally, individual nucleic acid template molecules can be from about 2 kb bases to about 40 kb. In a particular embodiment, nucleic acids are about 6 kb-10 kb fragments. Nucleic acid molecules may be single-stranded, double-stranded, or double stranded with single-stranded regions (for example, stem- and loop-structures).

A biological sample may be lysed, homogenized, or fractionated in the presence of a detergent or surfactant as needed. Suitable detergents may include an ionic detergent (e.g., sodium dodecyl sulfate or N-lauroylsarcosine) or a nonionic detergent (such as the polysorbate 80 sold under the trademark TWEEN by Uniqema Americas (Paterson, N.J.) or $C14H_{22}O(C_2H_4)_n$, known as TRITON X-100). Once a nucleic acid is extracted or isolated from the sample it may be amplified.

Amplification refers to production of additional copies of a nucleic acid sequence and is generally carried out using polymerase chain reaction (PCR) or other technologies known in the art. The amplification reaction may be any amplification reaction known in the art that amplifies nucleic acid molecules such as PCR. Other amplification reactions include nested PCR, PCR-single strand conformation polymorphism, ligase chain reaction, strand displacement amplification and restriction fragments length polymorphism, transcription based amplification system, rolling circle amplification, and hyper-branched rolling circle amplification, quantitative PCR, quantitative fluorescent PCR (QF-PCR), multiplex fluorescent PCR (MF-PCR), real time PCR (RTPCR), restriction fragment length polymorphism PCR (PCR-RFLP), in situ rolling circle amplification (RCA), bridge PCR, picotiter PCR, emulsion PCR, transcription amplification, self-sustained sequence replication, consensus sequence primed PCR, arbitrarily primed PCR, degenerate oligonucleotide-primed PCR, and nucleic acid based sequence amplification (NABSA). Amplification methods that can be used include those described in U.S. Pat. Nos. 5,242,794; 5,494,810; 4,988,617; and 6,582,938. In certain embodiments, the amplification reaction is PCR as described, for example, U.S. Pat. Nos. 4,683,195; and 4,683,202, hereby incorporated by reference. Primers for PCR, sequencing, and other methods can be prepared by cloning, direct chemical synthesis, and other methods known in the art. Primers can also be obtained from commercial sources such as Eurofins MWG Operon (Huntsville, Ala.) or Life Technologies (Carlsbad, Calif.).

Bar code sequences can be designed such that each sequence is correlated to a particular portion of nucleic acid, allowing sequence reads to be correlated back to the portion from which they came. Methods of designing sets of bar code sequences are shown for example in U.S. Pat. No. 6,235,475, the contents of which are incorporated by reference herein in their entirety. In certain embodiments, the bar code sequences range from about 5 nucleotides to about 15 nucleotides. In a particular embodiment, the bar code sequences range from about 4 nucleotides to about 7 nucleotides. Methods for designing sets of bar code sequences and other methods for attaching bar code sequences are shown in U.S. Pat. Nos. 7,544,473; 7,537,897; 7,393,665; 6,352,828; 6,172,218; 6,172,214; 6,150,516; 6,138,077; 5,863,722; 5,846,719; 5,695,934; and 5,604,097, each incorporated by reference.

Sequencing may be by any method known in the art. DNA sequencing techniques include classic dideoxy sequencing reactions (Sanger method) using labeled terminators or primers and gel separation in slab or capillary, sequencing by synthesis using reversibly terminated labeled nucleotides, pyrosequencing, 454 sequencing, Illumina/Solexa sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD sequencing. Sequencing of separated molecules has more recently been demonstrated by sequential or single extension reactions using polymerases or ligases as well as by single or sequential differential hybridizations with libraries of probes.

A sequencing technique that can be used includes, for example, use of sequencing-by-synthesis systems sold under the trademarks GS JUNIOR, GS FLX+ and 454 SEQUENCING by 454 Life Sciences, a Roche company (Branford, Conn.), and described by Margulies, M. et al., Genome sequencing in micro-fabricated high-density picotiter reactors, Nature, 437:376-380 (2005); U.S. Pat. Nos. 5,583,024; 5,674,713; and 5,700,673, the contents of which are incorporated by reference herein in their entirety. 454 sequencing involves two steps. In the first step of those systems, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (pico-liter sized). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is detected and analyzed.

Another example of a DNA sequencing technique that can be used is SOLiD technology by Applied Biosystems from Life Technologies Corporation (Carlsbad, Calif.). In SOLiD sequencing, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is removed and the process is then repeated.

Another example of a DNA sequencing technique that can be used is ion semiconductor sequencing using, for example, a system sold under the trademark ION TORRENT by Ion Torrent by Life Technologies (South San Francisco, Calif.). Ion semiconductor sequencing is described, for example, in Rothberg, et al., An integrated semiconductor device enabling non-optical genome sequencing, Nature 475:348-352 (2011); U. S. Pub. 2010/0304982; U.S. Pub. 2010/0301398; U.S. Pub. 2010/0300895; U.S. Pub. 2010/0300559; and U.S. Pub. 2009/0026082, the contents of each of which are incorporated by reference in their entirety.

Another example of a sequencing technology that can be used is Illumina sequencing. Illumina sequencing is based on the amplification of DNA on a solid surface using fold-back PCR and anchored primers. Genomic DNA is fragmented, and adapters are added to the 5' and 3' ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection and identification steps are repeated. Sequencing according to this technology is described in U.S. Pat. Nos. 7,960,120; 7,835,871; 7,232,656; 7,598,035; 6,911,345; 6,833,246; 6,828,100; 6,306,597; 6,210,891; U.S. Pub. 2011/0009278; U.S. Pub. 2007/0114362; U.S. Pub. 2006/0292611; and U.S. Pub. 2006/0024681, each of which are incorporated by reference in their entirety.

Another example of a sequencing technology that can be used includes the single molecule, real-time (SMRT) technology of Pacific Biosciences (Menlo Park, Calif.). In SMRT, each of the four DNA bases is attached to one of four different fluorescent dyes. These dyes are phospholinked. A single DNA polymerase is immobilized with a single molecule of template single stranded DNA at the bottom of a zero-mode waveguide (ZMW). It takes several milliseconds to incorporate a nucleotide into a growing strand. During this time, the fluorescent label is excited and produces a fluorescent signal, and the fluorescent tag is cleaved off. Detection of the corresponding fluorescence of the dye indicates which base was incorporated. The process is repeated.

Another example of a sequencing technique that can be used is nanopore sequencing (Soni & Meller, 2007, Progress toward ultrafast DNA sequence using solid-state nanopores, Clin Chem 53(11):1996-2001). A nanopore is a small hole, of the order of 1 nanometer in diameter. Immersion of a nanopore in a conducting fluid and application of a potential across it results in a slight electrical current due to conduction of ions through the nanopore. The amount of current which flows is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore represents a reading of the DNA sequence.

Another example of a sequencing technique that can be used involves using a chemical-sensitive field effect transistor (chemFET) array to sequence DNA (for example, as described in U.S. Pub. 2009/0026082). In one example of the technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be detected by a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

Another example of a sequencing technique that can be used involves using an electron microscope as described, for example, by Moudrianakis, E. N. and Beer M., in Base sequence determination in nucleic acids with the electron microscope, III. Chemistry and microscopy of guanine-labeled DNA, PNAS 53:564-71 (1965). In one example of the technique, individual DNA molecules are labeled using metallic labels that are distinguishable using an electron microscope. These molecules are then stretched on a flat surface and imaged using an electron microscope to measure sequences.

Sequencing according to embodiments of the disclosure generates a plurality of reads. Reads according to the disclosure generally include sequences of nucleotide data less than about 150 bases in length, or less than about 90 bases in length. In certain embodiments, reads are between about 80 and about 90 bases, e.g., about 85 bases in length. In some embodiments, methods of the disclosure are applied to very short reads, i.e., less than about 50 or about 30 bases in length. Sequence read data can include the sequence data as well as meta information. Sequence read data can be stored in any suitable file format including, for example, VCF files, FASTA files or FASTQ files, as are known to those of skill in the art.

FASTA is originally a computer program for searching sequence databases and the name FASTA has come to also refer to a standard file format. See Pearson & Lipman, 1988, Improved tools for biological sequence comparison, PNAS 85:2444-2448. A sequence in FASTA format begins with a single-line description, followed by lines of sequence data. The description line is distinguished from the sequence data by a greater-than (">") symbol in the first column. The word following the ">" symbol is the identifier of the sequence, and the rest of the line is the description (both are optional). There should be no space between the ">" and the first letter of the identifier. It is recommended that all lines of text be shorter than 80 characters. The sequence ends if another line starting with a ">" appears; this indicates the start of another sequence.

The FASTQ format is a text-based format for storing both a biological sequence (usually nucleotide sequence) and its corresponding quality scores. It is similar to the FASTA format but with quality scores following the sequence data. Both the sequence letter and quality score are encoded with a single ASCII character for brevity. The FASTQ format is a de facto standard for storing the output of high throughput sequencing instruments such as the Illumina Genome Analyzer. Cock et al., 2009, The Sanger FASTQ file format for sequences with quality scores, and the Solexa/Illumina FASTQ variants, Nucleic Acids Res 38(6):1767-1771.

For FASTA and FASTQ files, meta information includes the description line and not the lines of sequence data. In some embodiments, for FASTQ files, the meta information includes the quality scores. For FASTA and FASTQ files, the sequence data begins after the description line and is present typically using some subset of IUPAC ambiguity codes optionally with "-". In a preferred embodiment, the sequence data will use the A, T, C, G, and N characters, optionally including "-" or U as-needed (e.g., to represent gaps or uracil).

As discussed above and elsewhere, the volume of output of NGS instruments is increasing. See, e.g., Pinho & Pratas, 2013, MFCompress: a compression tool for FASTA and multi-FASTA data, Bioinformatics 30(1):117-8; Deorowicz & Grabowski, 2013, Data compression for sequencing data, Alg Mol Bio 8:25; Balzer et al., 2013, Filtering duplicate reads from 454 pyrosequencing data, Bioinformatics 29(7): 830-836; Xu et al., 2012, FastUniq: A fast de novo duplicates removal tool for paired short reads, PLoS One 7(12): e52249; Bonfield and Mahoney, 2013, Compression of FASTQ and SAM format sequencing data, PLoS One 8(3): e59190; and Veeneman et al., 2012, Oculus: faster sequence alignment by streaming read compression, BMC Bioinformatics 13:297. The amount of data generated by NGS technologies raises challenges in storing and transferring files containing such sequencing information. Accordingly, methods and systems of the disclosure can be used for storing information such as the large volumes of sequence data contained in FASTA or FASTQ files (FASTA/Q files) originating from nucleic acid sequencing technologies.

In some embodiments, the sequence read and/or output files are stored as plain text files (e.g., using encoding such as ASCII; ISO/IEC 646; EBCDIC; UTF-8; or UTF-16). A computer system provided by the disclosure may include a text editor program capable of opening the plain text files. A text editor program may refer to a computer program capable of presenting contents of a text file (such as a plain text file) on a computer screen, allowing a human to edit the text (e.g., using a monitor, keyboard, and mouse). Exemplary text editors include, without limit, Microsoft Word, emacs, pico, vi, BBEdit, and TextWrangler. Preferably, the text editor program is capable of displaying the plain text files on a computer screen, showing the meta information and the sequence reads in a human-readable format (e.g., not binary encoded In some embodiments, any or all of the steps of the disclosure are automated. For example, a Perl script or shell script can be written to invoke any of the various programs discussed above (see, e.g., Tisdall, Mastering Perl for Bioinformatics, O'Reilly & Associates, Inc., Sebastopol, C A 2003; Michael, R., Mastering Unix Shell Scripting, Wiley Publishing, Inc., Indianapolis, Ind. 2003). Alternatively, methods of the disclosure may be embodied wholly or partially in one or more dedicated programs, for example, each optionally written in a compiled language such as C++ then compiled and distributed as a binary. Methods of the disclosure may be implemented wholly or in part as modules within, or by invoking functionality within, existing sequence analysis platforms. In certain embodiments, methods of the disclosure include a number of steps that are all invoked automatically responsive to a single starting queue (e.g., one or a combination of triggering events sourced from human activity, another computer program, or a machine). Thus, the disclosure provides methods in which any or the steps or any combination of the steps can occur automatically responsive to a queue. Automatically generally means without intervening human input, influence, or interaction (i.e., responsive only to original or pre-queue human activity).

The disclosure also encompasses various forms of output, which includes an accurate and sensitive interpretation of the subject nucleic acid. The output can be provided in the format of a computer file. In certain embodiments, the output is a FASTA file, FASTQ file, or VCF file. Output may be processed to produce a text file, or an XML file containing sequence data such as a sequence of the nucleic acid aligned to a sequence of the reference genome. In other embodiments, processing yields output containing coordinates or a string describing one or more mutations in the subject nucleic acid relative to the reference genome. Alignment strings known in the art include Simple UnGapped Alignment Report (SUGAR), Verbose Useful Labeled Gapped Alignment Report (VULGAR), and Compact Idiosyncratic Gapped Alignment Report (CIGAR) (Ning, Z., et al., Genome Research 11(10):1725-9 (2001)). These strings are implemented, for example, in the Exonerate sequence alignment software from the European Bioinformatics Institute (Hinxton, UK).

In some embodiments, a sequence alignment is produced—such as, for example, a sequence alignment map (SAM) or binary alignment map (BAM) file—comprising a CIGAR string (the SAM format is described, e.g., in Li et al., The Sequence Alignment/Map format and SAMtools, Bioinformatics, 2009, 25(16):2078-9). In some embodiments, CIGAR displays or includes gapped alignments one-per-line. CIGAR is a compressed pairwise alignment format reported as a CIGAR string. A CIGAR string is useful for representing long (e.g. genomic) pairwise alignments. A CIGAR string is used in SAM format to represent alignments of reads to a reference genome sequence.

A CIGAR string follows an established motif. Each character is preceded by a number, giving the base counts of the event. Characters used can include M, I, D, N, and S (M=match; I=insertion; D=deletion; N=gap; S=substitution). The CIGAR string defines the sequence of matches/mismatches and deletions (or gaps). For example, the CIGAR string 2MD3M2D2M will mean that the alignment contains 2 matches, 1 deletion (number 1 is omitted in order to save some space), 3 matches, 2 deletions and 2 matches.

As contemplated by the disclosure, the functions described above can be implemented using a system of the disclosure that includes software, hardware, firmware, hardwiring, or any combinations of these. Features implementing functions can also be physically located at various positions, including being distributed such that portions of functions are implemented at different physical locations.

As one skilled in the art would recognize as necessary or best-suited for performance of the methods of the disclosure, a computer system or machines of the disclosure include one or more processors (e.g., a central processing unit (CPU) a graphics processing unit (GPU) or both), a main memory and a static memory, which communicate with each other via a bus.

Figure 12:
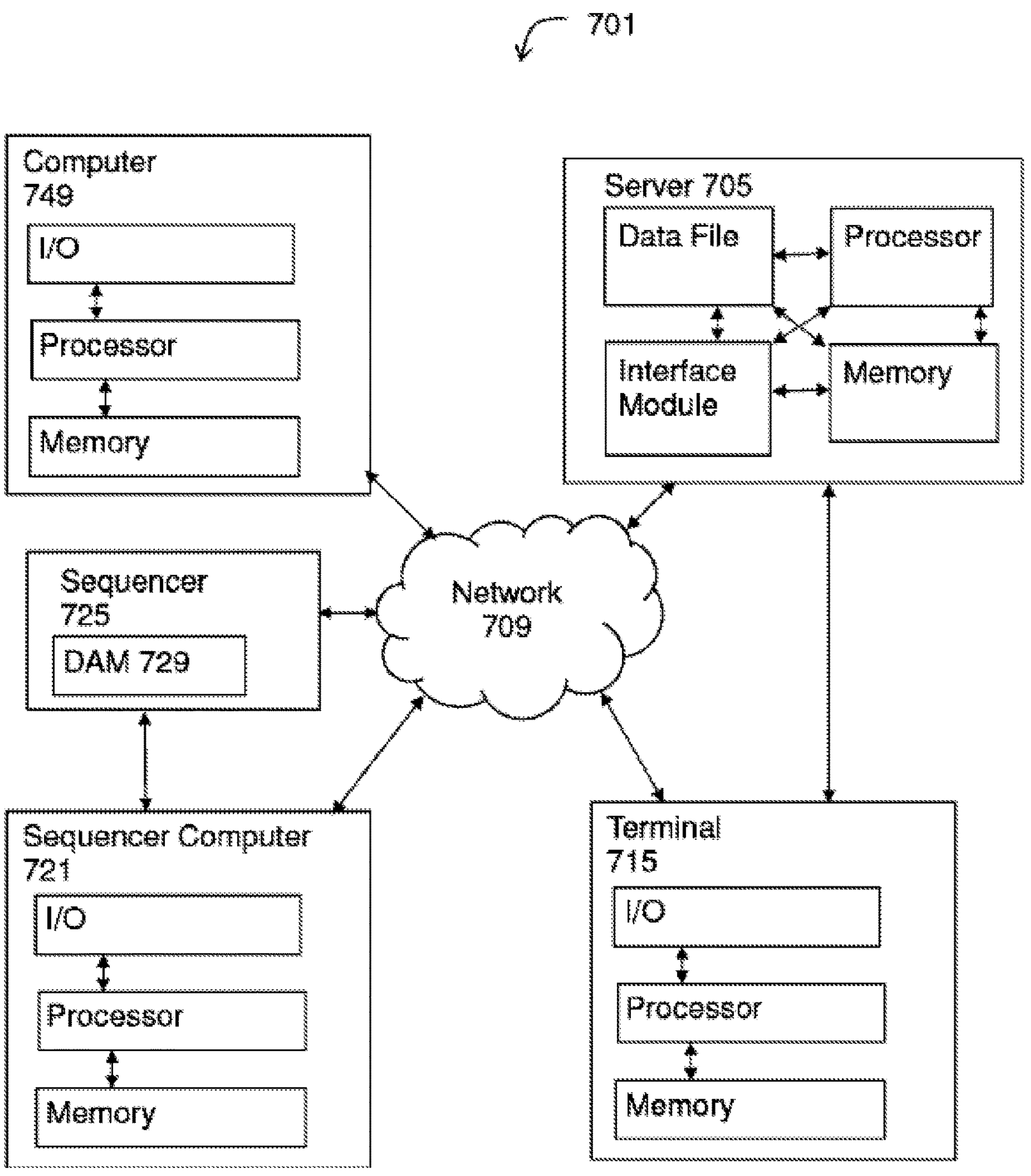
FIG. 12 diagrams a system of the disclosure.

FIG. 12 diagrams a system 701 suitable for performing methods of the disclosure. As shown in FIG. 12, system 701 may include one or more of a server computer 705, a terminal 715, a sequencer 715, a sequencer computer 721, a computer 749, or any combination thereof. Each such computer device may communicate via network 709. Sequencer 725 may optionally include or be operably coupled to its own, e.g., dedicated, sequencer computer 721 (including any input/output mechanisms (I/O), processor, and memory such as, e.g., dynamic random-access memory DRAM or DAM 729). Additionally or alternatively, sequencer 725 may be operably coupled to a server 705 or computer 749 (e.g., laptop, desktop, or tablet) via network 709. Computer 749 includes one or more processor, memory, and I/O. Where methods of the disclosure employ a client/server architecture, any steps of methods of the disclosure may be performed using server 705, which includes one or more of processor, memory, and I/O, capable of obtaining data, instructions, etc., or providing results via an interface module or providing results as a file. Server 705 may be engaged over network 709 through computer 749 or terminal 715, or server 705 may be directly connected to terminal 715. Terminal 715 is preferably a computer device. A computer according to the disclosure preferably includes one or more processor coupled to an I/O mechanism and memory.

A processor may be provided by one or more processors including, for example, one or more of a single core or multi-core processor (e.g., AMD Phenom II X2, Intel Core Duo, AMD Phenom II X4, Intel Core i5, Intel Core i& Extreme Edition 980X, or Intel Xeon E7-2820).

An I/O mechanism may include a video display unit (e.g., a liquid crystal display (LCD) or a cathode ray tube (CRT)), an alphanumeric input device (e.g., a keyboard), a cursor control device (e.g., a mouse), a disk drive unit, a signal generation device (e.g., a speaker), an accelerometer, a microphone, a cellular radio frequency antenna, and a network interface device (e.g., a network interface card (NIC), Wi-Fi card, cellular modem, data jack, Ethernet port, modem jack, HDMI port, mini-HDMI port, USB port), touchscreen (e.g., CRT, LCD, LED, AMOLED, Super AMOLED), pointing device, trackpad, light (e.g., LED), light/image projection device, or a combination thereof.

Memory according to the disclosure refers to a non-transitory memory which is provided by one or more tangible devices which preferably include one or more machine-readable medium on which is stored one or more sets of instructions (e.g., software) embodying any one or more of the methodologies or functions described herein. The software may also reside, completely or at least partially, within the main memory, processor, or both during execution thereof by a computer within system 501, the main memory and the processor also constituting machine-readable media. The software may further be transmitted or received over a network via the network interface device.

While the machine-readable medium can in an exemplary embodiment be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that cause the machine to perform any one or more of the methodologies of the present disclosure. Memory may be, for example, one or more of a hard disk drive, solid state drive (SSD), an optical disc, flash memory, zip disk, tape drive, "cloud" storage location, or a combination thereof. In certain embodiments, a device of the disclosure includes a tangible, non-transitory computer readable medium for memory. Exemplary devices for use as memory include semiconductor memory devices, (e.g., EPROM, EEPROM, solid state drive (SSD), and flash memory devices e.g., SD, micro SD, SDXC, SDIO, SDHC cards); magnetic disks, (e.g., internal hard disks or removable disks); and optical disks (e.g., CD and DVD disks).

Different ways of assembling a contig and generating a consensus sequence are discussed below.

A contig, generally, refers to the relationship between or among a plurality of segments of nucleic acid sequences, e.g., reads. Where sequence reads overlap, a contig can be represented as a layered image of overlapping reads. A contig is not defined by, nor limited to, any particular visual arrangement nor any particular arrangement within, for example, a text file or a database. A contig generally includes sequence data from a number of reads organized to correspond to a portion of a sequenced nucleic acid. A contig can include assembly results—such as a set of reads or information about their positions relative to each other or to a reference—displayed or stored. A contig can be structured as a grid, in which rows are individual sequence reads and columns include the base of each read that is presumed to align to that site. A consensus sequence can be made by identifying the predominant base in each column of the assembly. A contig according to the invention can include the visual display of reads showing them overlap (or not, e.g., simply abutting) one another. A contig can include a set of coordinates associated with a plurality of reads and giving the position of the reads relative to each other. A contig can include data obtained by transforming the sequence data of reads. For example, a Burrows-Wheeler transformation can be performed on the reads, and a contig can include the transformed data without necessarily including the untransformed sequences of the reads. A Burrows-Wheeler transform of nucleotide sequence data is described in U.S. Pub. 2005/0032095, herein incorporated by reference in its entirety.

Reads can be assembled into contigs by any method known in the art. Algorithms for the de novo assembly of a plurality of sequence reads are known in the art, though such known algorithms have been improved upon herein, for the structured sequence read inputs currently described (individual sequence elements derived from a library of high complexity, flanked by linker sequences of low complexity, present as a repeating series (chimeric array) within each long sequence read of a broader population of long sequence reads).

One algorithm for assembling sequence reads is known as overlap consensus assembly. Overlap consensus assembly uses the overlap between sequence reads to create a link between them. The reads are generally linked by regions that overlap enough that non-random overlap is assumed. Linking together reads in this way produces a contig or an overlap graph in which each node corresponds to a read and an edge represents an overlap between two reads. Assembly with overlap graphs is described, for example, in U.S. Pat. No. 6,714,874.

In some embodiments, de novo assembly proceeds according to so-called greedy algorithms. For assembly according to greedy algorithms, one of the reads of a group of reads is selected, and it is paired with another read with which it exhibits a substantial amount of overlap—generally it is paired with the read with which it exhibits the most overlap of all of the other reads. Those two reads are merged to form a new read sequence, which is then put back in the group of reads and the process is repeated. Assembly according to a greedy algorithm is described, for example, in Schatz, et al., Genome Res., 20:1165-1173 (2010) and U.S. Pub. 2011/0257889, each of which is hereby incorporated by reference in its entirety.

In other embodiments, assembly proceeds by pairwise alignment, for example, exhaustive or heuristic (e.g., not exhaustive) pairwise alignment. Alignment, generally, is discussed in more detail below. Exhaustive pairwise alignment, sometimes called a "brute force" approach, calculates an alignment score for every possible alignment between every possible pair of sequences among a set. Assembly by heuristic multiple sequence alignment ignores certain mathematically unlikely combinations and can be computationally faster. One heuristic method of assembly by multiple sequence alignment is the so-called "divide-and-conquer" heuristic, which is described, for example, in U.S. Pub. 2003/0224384. Another heuristic method of assembly by multiple sequence alignment is progressive alignment, as implemented by the program ClustalW (see, e.g., Thompson, et al., Nucl. Acids. Res., 22:4673-80 (1994)). Assembly by multiple sequence alignment in general is discussed in Lecompte, O., et al., Gene 270:17-30 (2001); Mullan, L. J., Brief Bioinform., 3:303-5 (2002); Nicholas, H. B. Jr., et al., Biotechniques 32:572-91 (2002); and Xiong, G., Essential Bioinformatics, 2006, Cambridge University Press, New York, N.Y.

Assembly by alignment can proceed by aligning reads to each other or by aligning reads to a reference. For example, by aligning each read, in turn, to a reference genome, all of the reads are positioned in relationship to each other to create the assembly.

One method of assembling reads into contigs involves making a de Bruijn graph. De Bruijn graphs reduce the computation effort by breaking reads into smaller sequences of DNA, called k-mers, where the parameter k denotes the length in bases of these sequences. In a de Bruijn graph, all reads are broken into k-mers (all subsequences of length k within the reads) and a path between the k-mers is calculated. In assembly according to this method, the reads are represented as a path through the k-mers. The de Bruijn graph captures overlaps of length k−1 between these k-mers and not between the actual reads. Thus, for example, the sequencing CATGGA could be represented as a path through the following 2-mers: CA, AT, TG, GG, and GA. The de Bruijn graph approach handles redundancy well and makes the computation of complex paths tractable. By reducing the entire data set down to k-mer overlaps, the de Bruijn graph reduces the high redundancy in short-read data sets. The maximum efficient k-mer size for a particular assembly is determined by the read length as well as the error rate. The value of the parameter k has significant influence on the quality of the assembly. Estimates of good values can be made before the assembly, or the optimal value can be found by testing a small range of values. Assembly of reads using de Bruijn graphs is described in U.S. Pub. 2011/0004413, U.S. Pub. 2011/0015863, and U.S. Pub. 2010/0063742, each of which are herein incorporated by reference in their entirety.

Other methods of assembling reads into contigs according to the invention are possible. For example, the reads may contain barcode information inserted into template nucleic acid during sequencing. In certain embodiments, reads are assembled into contigs by reference to the barcode information. For example, the barcodes can be identified and the reads can be assembled by positioning the barcodes together.

Assembly of reads into contigs is further discussed in Husemann, P. and Stoye, J, Phylogenetic Comparative Assembly, 2009, Algorithms in Bioinformatics: 9th International Workshop, pp. 145-156, Salzberg, S., and Warnow, T., Eds. Springer-Verlag, Berlin Heidelberg. Some exemplary methods for assembling reads into contigs are described, for example, in U.S. Pat. No. 6,223,128, U.S. Pub. 2009/0298064, U.S. Pub. 2010/0069263, and U.S. Pub. 2011/0257889, each of which is incorporated by reference herein in its entirety.

Computer programs for assembling reads are known in the art. Such assembly programs can run on a single general-purpose computer, on a cluster or network of computers, or on a specialized computing devices dedicated to sequence analysis.

Assembly can be implemented, for example, by the program 'The Short Sequence Assembly by k-mer search and 3' read Extension' (SSAKE), from Canada's Michael Smith Genome Sciences Centre (Vancouver, B.C., CA) (see, e.g., Warren, R., et al., Bioinformatics, 23:500-501 (2007)). S SAKE cycles through a table of reads and searches a prefix tree for the longest possible overlap between any two sequences. SSAKE clusters reads into contigs.

Another read assembly program is Forge Genome Assembler, written by Darren Platt and Dirk Evers and available through the SourceForge web site maintained by Geeknet (Fairfax, Va.) (see, e.g., DiGuistini, S., et al., Genome Biology, 10:R94 (2009)). Forge distributes its computational and memory consumption to multiple nodes, if available, and has therefore the potential to assemble large sets of reads. Forge was written in C++ using the parallel MPI library. Forge can handle mixtures of reads, e.g., Sanger, 454, and Illumina reads.

Assembly through multiple sequence alignment can be performed, for example, by the program Clustal Omega, (Sievers F., et al., Mol Syst Biol 7 (2011)), ClustalW, or ClustalX (Larkin M. A., et al., Bioinformatics, 23, 2947-2948 (2007)) available from University College Dublin (Dublin, Ireland).

Another exemplary read assembly program known in the art is Velvet, available through the web site of the European Bioinformatics Institute (Hinxton, UK) (Zerbino D. R. et al., Genome Research 18(5):821-829 (2008)). Velvet implements an approach based on de Bruijn graphs, uses information from read pairs, and implements various error correction steps.

Read assembly can be performed with the programs from the package SOAP, available through the website of Beijing Genomics Institute (Beijing, Conn.) or BGI Americas Corporation (Cambridge, Mass.). For example, the SOAPdenovo program implements a de Bruijn graph approach. SOAPS/GPU aligns short reads to a reference sequence.

Another read assembly program is ABySS, from Canada's Michael Smith Genome Sciences Centre (Vancouver, B. C., CA) (Simpson, J. T., et al., Genome Res., 19(6):1117-23 (2009)). ABySS uses the de Bruijn graph approach and runs in a parallel environment.

Read assembly can also be done by Roche's GS De Novo Assembler, known as gsAssembler or Newbler (NEW assemBLER), which is designed to assemble reads from the Roche 454 sequencer (described, e.g., in Kumar, S. et al., Genomics 11:571 (2010) and Margulies, et al., Nature 437:376-380 (2005)). Newbler accepts 454 Flx Standard reads and 454 Titanium reads as well as single and paired-end reads and optionally Sanger reads. Newbler is run on Linux, in either 32 bit or 64 bit versions. Newbler can be accessed via a command-line or a Java-based GUI interface.

Cortex, created by Mario Caccamo and Zamin Iqbal at the University of Oxford, is a software framework for genome analysis, including read assembly. Cortex includes cortex_con for consensus genome assembly, used as described in Spanu, P. D., et al., Science 330(6010):1543-46 (2010). Cortex includes cortex var for variation and population assembly, described in Iqbal, et al., De novo assembly and genotyping of variants using colored de Bruijn graphs, Nature Genetics (in press), and used as described in Mills, R. E., et al., Nature 470:59-65 (2010). Cortex is available through the creators' web site and from the SourceForge web site maintained by Geeknet (Fairfax, Va.).

Other read assembly programs include RTG Investigator from Real Time Genomics, Inc. (San Francisco, Calif.); iAssembler (Zheng, et al., BMC Bioinformatics 12:453 (2011)); TgiCL Assembler (Pertea, et al., Bioinformatics 19(5):651-52 (2003)); Maq (Mapping and Assembly with Qualities) by Heng Li, available for download through the SourceForge website maintained by Geeknet (Fairfax, Va.); MIRA3 (Mimicking Intelligent Read Assembly), described in Chevreux, B., et al., Genome Sequence Assembly Using Trace Signals and Additional Sequence Information, 1999, Computer Science and Biology: Proceedings of the German Conference on Bioinformatics (GCB) 99:45-56; PGA4genomics (described in Zhao F., et al., Genomics. 94(4):284-6 (2009)); and Phrap (described, e.g., in de la Bastide, M. and McCombie, W. R., Current Protocols in Bioinformatics, 17:11.4.1-11.4.15 (2007)). CLC cell is a de Bruijn graph-based computer program for read mapping and de novo assembly of NGS reads available from CLC bio Germany (Muehltal, Germany).

Assembly of reads produces one or more contigs. In the case of a homozygous or single target sequencing, a single contig will be produced. In the case of a heterozygous diploid target, a rare somatic mutation, or a mixed sample, for example, two or more contigs can be produced. Each contig includes information from the reads that make up that contig.

Assembling the reads into contigs is conducive to producing a consensus sequence corresponding to each contig. In certain embodiments, a consensus sequence refers to the most common, or predominant, nucleotide at each position from among the assembled reads. A consensus sequence can represent an interpretation of the sequence of the nucleic acid represented by that contig.

Alignment, as used herein, generally involves placing one sequence along another sequence, iteratively introducing gaps along each sequence, scoring how well the two sequences match, and preferably repeating for various positions along the reference. The best-scoring match is deemed to be the alignment and represents an inference about the historical relationship between the sequences. In an alignment, a base in the read alongside a non-matching base in the reference indicates that a substitution mutation has occurred at that point. Similarly, where one sequence includes a gap alongside a base in the other sequence, an insertion or deletion mutation (an "indel") is inferred to have occurred. When it is desired to specify that one sequence is being aligned to one other, the alignment is sometimes called a pairwise alignment. Multiple sequence alignment generally refers to the alignment of two or more sequences, including, for example, by a series of pairwise alignments.

In some embodiments, scoring an alignment involves setting values for the probabilities of substitutions and indels. When individual bases are aligned, a match or mismatch contributes to the alignment score by a substitution probability, which could be, for example, 1 for a match and 0.33 for a mismatch. An indel deducts from an alignment score by a gap penalty, which could be, for example, −1. Gap penalties and substitution probabilities can be based on empirical knowledge or a priori assumptions about how sequences mutate. Their values affect the resulting alignment. Particularly, the relationship between the gap penalties and substitution probabilities influences whether substitutions or indels will be favored in the resulting alignment.

Stated formally, an alignment represents an inferred relationship between two sequences, x and y. For example, in some embodiments, an alignment A of sequences x and y maps x and y respectively to another two strings x' and y' that may contain spaces such that: (i) $|x'|=|y'|$; (ii) removing spaces from x' and y' should get back x and y, respectively; and (iii) for any i, x'[i]; and y'[i] cannot be both spaces.

A gap is a maximal substring of contiguous spaces in either x' or y'. An alignment A can include the following three kinds of regions: (i) matched pair (e.g., $x'[i]=y'[i]$; (ii) mismatched pair, (e.g., $x'[i]\neq y'[i]$ and both are not spaces); or (iii) gap (e.g., either x'[i . . . j] or y'[i . . . j] is a gap). In certain embodiments, only a matched pair has a high positive score a. In some embodiments, a mismatched pair generally has a negative score b and a gap of length r also has a negative score g+rs where $g, s<0$. For DNA, one common scoring scheme (e.g. used by BLAST) makes score a=1, score b=−3, g=−5 and s=−2. The score of the alignment A is the sum of the scores for all matched pairs, mismatched pairs and gaps. The alignment score of x and y can be defined as the maximum score among all possible alignments of x and y.

In some embodiments, any pair has a score a defined by a 4×4 matrix B of substitution probabilities. For example, $B(i,i)=1$ and $0<B(i,j)i< >j<1$ is one possible scoring system. For instance, where a transition is thought to be more biologically probable than a transversion, matrix B could include B(C,T)=0.7 and B(A,T)=0.3, or any other set of values desired or determined by methods known in the art.

Alignment according to some embodiments of the invention includes pairwise alignment. A pairwise alignment, generally, involves—for sequence Q (query) having m characters and a reference genome T (target) of n characters—finding and evaluating possible local alignments between Q and T. For any $1\leq i\leq n$ and $1\leq j\leq m$, the largest possible alignment score of T[h . . . i] and Q[k . . . j], where $h\leq i$ and $k\leq j$, is computed (i.e. the best alignment score of any substring of T ending at position i and any substring of Q ending at position j). This can include examining all substrings with cm characters, where c is a constant depending on a similarity model, and aligning each substring separately with Q. Each alignment is scored, and the alignment with the preferred score is accepted as the alignment. In some embodiments an exhaustive pairwise alignment is performed, which generally includes a pairwise alignment as described above, in which all possible local alignments (optionally subject to some limiting criteria) between Q and T are scored.

In some embodiments, pairwise alignment proceeds according to dot-matrix methods, dynamic programming methods, or word methods. Dynamic programming methods generally implement the Smith-Waterman (SW) algorithm or the Needleman-Wunsch (NW) algorithm. Alignment according to the NW algorithm generally scores aligned characters according to a similarity matrix S(a,b) (e.g., such as the aforementioned matrix B) with a linear gap penalty d. Matrix S(a,b) generally supplies substitution probabilities. The SW algorithm is similar to the NW algorithm, but any negative scoring matrix cells are set to zero. The SW and NW algorithms, and implementations thereof, are described in more detail in U.S. Pat. No. 5,701,256 and U.S. Pub. 2009/0119313, both herein incorporated by reference in their entirety. Computer programs known in the art for implementing these methods are described in more detail below.

An alignment according to the invention can be performed using any suitable computer program known in the art.

One exemplary alignment program, which implements a BWT approach, is Burrows-Wheeler Aligner (BWA) available from the SourceForge web site maintained by Geeknet (Fairfax, Va.). BWA can align reads, contigs, or consensus sequences to a reference. BWT occupies 2 bits of memory per nucleotide, making it possible to index nucleotide sequences as long as 4G base pairs with a typical desktop or laptop computer. The pre-processing includes the construction of BWT (i.e., indexing the reference) and the supporting auxiliary data structures.

BWA implements two different algorithms, both based on BWT. Alignment by BWA can proceed using the algorithm bwa-short, designed for short queries up to ~200 bp with low error rate (<3%) (Li H. and Durbin R. Bioinformatics, 25:1754-60 (2009)). The second algorithm, BWA-SW, is designed for long reads with more errors (Li H. and Durbin R. (2010) Fast and accurate long-read alignment with Burrows-Wheeler Transform. Bioinformatics, Epub.). The BWA-SW component performs heuristic Smith-Waterman-like alignment to find high-scoring local hits. One skilled in the art will recognize that bwa-sw is sometimes referred to as "bwa-long", "bwa long algorithm", or similar. Such usage generally refers to BWA-SW.

An alignment program that implements a version of the Smith-Waterman algorithm is MUMmer, available from the SourceForge web site maintained by Geeknet (Fairfax, Va.). MUMmer is a system for rapidly aligning entire genomes, whether in complete or draft form (Kurtz, S., et al., Genome Biology, 5:R12 (2004); Delcher, A. L., et al., Nucl. Acids Res., 27:11 (1999)). For example, MUMmer 3.0 can find all 20-basepair or longer exact matches between a pair of 5-megabase genomes in 13.7 seconds, using 78 MB of memory, on a 2.4 GHz Linux desktop computer. MUMmer can also align incomplete genomes; it can easily handle the 100s or 1000s of contigs from a shotgun sequencing project, and will align them to another set of contigs or a genome using the NUCmer program included with the system. If the species are too divergent for a DNA sequence alignment to detect similarity, then the PROmer program can generate alignments based upon the six-frame translations of both input sequences.

Another exemplary alignment program according to embodiments of the invention is BLAT from Kent Informatics (Santa Cruz, Calif.) (Kent, W. J., Genome Research 4: 656-664 (2002)). BLAT (which is not BLAST) keeps an index of the reference genome in memory such as RAM. The index includes of all non-overlapping k-mers (except optionally for those heavily involved in repeats), where k=11 by default. The genome itself is not kept in memory. The index is used to find areas of probable homology, which are then loaded into memory for a detailed alignment.

Another alignment program is SOAP2, from Beijing Genomics Institute (Beijing, Conn.) or BGI Americas Corporation (Cambridge, Mass.). SOAP2 implements a 2-way BWT (Li et al., Bioinformatics 25(15):1966-67 (2009); Li, et al., Bioinformatics 24(5):713-14 (2008)).

Another program for aligning sequences is Bowtie (Langmead, et al., Genome Biology, 10:R25 (2009)). Bowtie indexes reference genomes by making a BWT.

Other exemplary alignment programs include: Efficient Large-Scale Alignment of Nucleotide Databases (ELAND) or the ELANDv2 component of the Consensus Assessment of Sequence and Variation (CASAVA) software (Illumina, San Diego, Calif.); RTG Investigator from Real Time Genomics, Inc. (San Francisco, Calif.); Novoalign from Novocraft (Selangor, Malaysia); Exonerate, European Bioinformatics Institute (Hinxton, UK) (Slater, G., and Birney, E., BMC Bioinformatics 6:31 (2005)), Clustal Omega, from University College Dublin (Dublin, Ireland) (Sievers F., et al., Mol Syst Biol 7, article 539 (2011)); ClustalW or ClustalX from University College Dublin (Dublin, Ireland) (Larkin M. A., et al., Bioinformatics, 23, 2947-2948 (2007)); and FASTA, European Bioinformatics Institute (Hinxton, UK) (Pearson W. R., et al., PNAS 85(8):2444-8 (1988); Lipman, D. J., Science 227(4693):1435-41 (1985).

Figure 13:
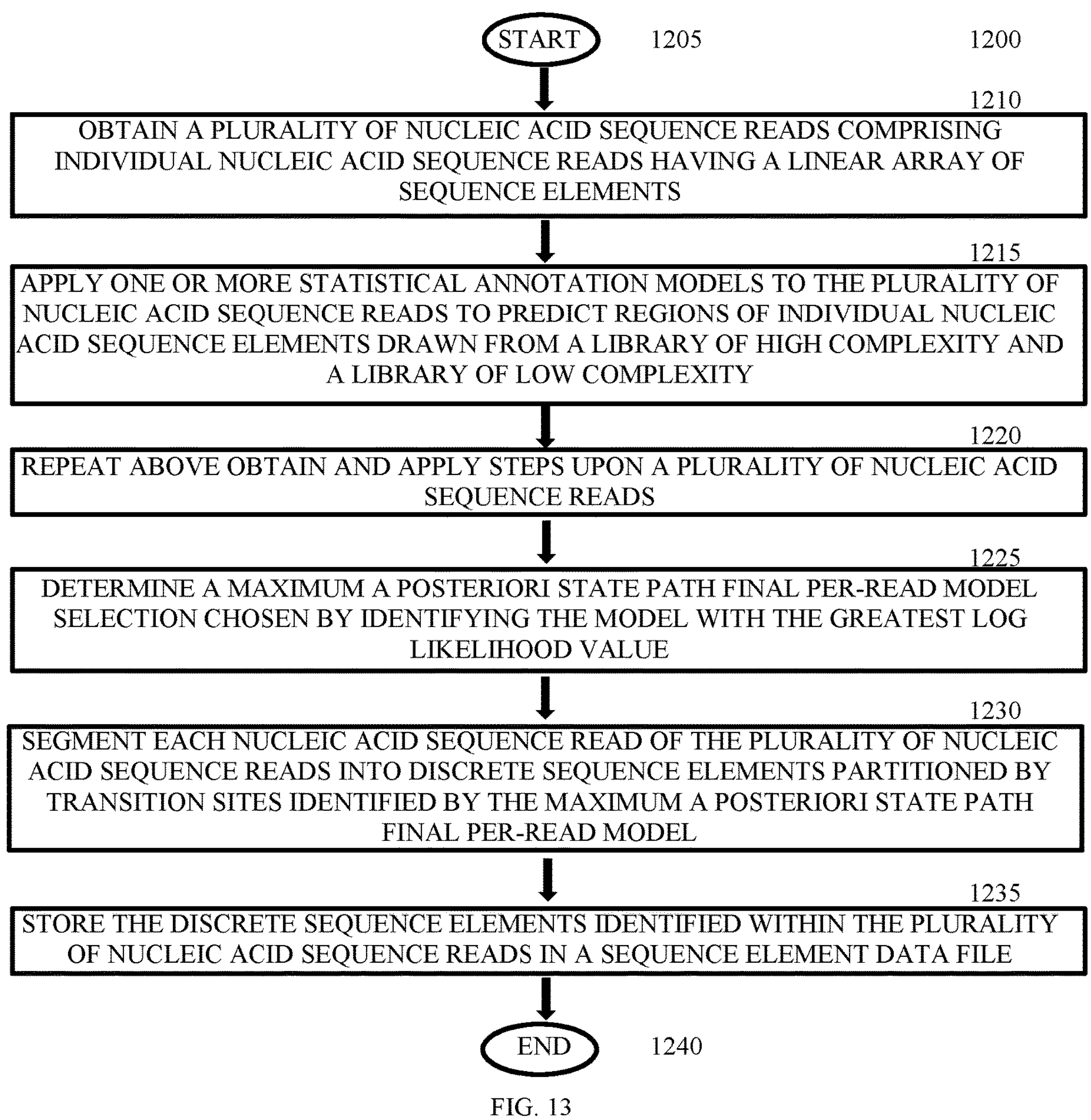
FIG. 13 illustrates an example procedure for determining a maximum state path in accordance with one or more embodiments of the disclosure.

FIG. 13 illustrates and example simplified procedure for determining a maximum state path in accordance with one or more embodiments of the disclosure. For example, a non-generic, specifically configured device (e.g., system 701) may perform procedure 1200 by executing stored instructions. The procedure 1200 may start at step 1205, and continue to step 1210 where, as described in detail above, a process may obtain a plurality of nucleic acid sequence reads that include individual nucleic acid sequence reads having a linear array of sequence elements. In embodiments, each nucleic acid sequence element drawn from a library of high complexity may be flanked either by one or more expected nucleic acid sequences of low complexity or by one or more expected nucleic acid sequence of low complexity and a sequence read terminus.

In step 1215, the process may apply one or more statistical annotation models to the plurality of nucleic acid sequence reads in order to predict regions of individual nucleic acid sequence elements drawn from a library of high complexity and a library of low complexity. In embodiments, the one or more statistical annotation models may include: i) a generative statistical alignment model for recognizing one or more expected nucleic acid sequences interspersed throughout a nucleic acid sequence read; or ii) a random statistical alignment model for recognizing sequences not known or drawn from a dictionary of sequences of high complexity. In embodiments, predicted transition sites are placed at the termini of each model and disallowed within internal positions in the generative statistical alignment model.

In step 1220, the previous 2 steps may be repeated upon a plurality of nucleic acid sequence reads. In step 1225, the process may then determine a maximum a posteriori state path final per-read model selection chosen by identifying the model with the greatest log likelihood value. In this way, the process may then apply the one or more statistical models to each nucleic acid sequence read of the plurality of nucleic acid sequence reads in both forward and reverse-complement orientations, and determine a maximum a posteriori state path Final per-read model selection chosen by identifying the model with the greatest log likelihood value.

In step 1230, the process may then segment each nucleic acid sequence read of the plurality of nucleic acid sequence reads into discrete sequence elements partitioned by transition sites identified by the maximum a posteriori state path final per-read model, which may identify discrete sequence elements within the plurality of nucleic acid sequence reads.

In step 1235, the process may then store the discrete sequence elements identified within the plurality of nucleic acid sequence reads in a sequence element data file. The simplified procedure 1700 may illustratively end in step 1240, until a new process is initiated.

Kits

The instant disclosure also provides kits containing agents of this disclosure for use in the methods of the present disclosure. Kits of the instant disclosure may include one or more containers comprising an agent and/or composition of this disclosure. In some embodiments, the kits further include instructions for use in accordance with the methods of this disclosure.

Instructions supplied in the kits of the instant disclosure are typically written instructions on a label or package insert (e.g., a paper sheet included in the kit), but machine-readable instructions (e.g., instructions carried on a magnetic or optical storage disk) are also acceptable. Instructions may be provided for practicing any of the methods described herein.

The kits of this disclosure are in suitable packaging. Suitable packaging includes, but is not limited to, vials, bottles, jars, flexible packaging (e.g., sealed Mylar or plastic bags), and the like. The container may further comprise a pharmaceutically active agent.

Kits may optionally provide additional components such as buffers and interpretive information. Normally, the kit comprises a container and a label or package insert(s) on or associated with the container.

The practice of the present disclosure employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, Molecular Cloning (Cold Spring Harbor Laboratory Press, Cold Spring Harbor, N.Y.); Sambrook et al., 1989, Molecular Cloning, 2nd Ed. (Cold Spring Harbor Laboratory Press, Cold Spring Harbor, N.Y.); Sambrook and Russell, 2001, Molecular Cloning, 3rd Ed. (Cold Spring Harbor Laboratory Press, Cold Spring Harbor, N.Y.); Ausubel et al., 1992), Current Protocols in Molecular Biology (John Wiley & Sons, including periodic updates); Glover, 1985, DNA Cloning (IRL Press, Oxford); Anand, 1992; Guthrie and Fink, 1991; Harlow and Lane, 1988, Antibodies, (Cold Spring Harbor Laboratory Press, Cold Spring Harbor, N.Y.); Jakoby and Pastan, 1979; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Riott, Essential Immunology, 6th Edition, Blackwell Scientific Publications, Oxford, 1988; Hogan et al., Manipulating the Mouse Embryo, (Cold Spring Harbor Laboratory Press, Cold Spring Harbor, N.Y., 1986); Westerfield, M., The zebrafish book. A guide for the laboratory use of zebrafish (*Danio rerio*), (4th Ed., Univ. of Oregon Press, Eugene, 2000).

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Reference will now be made in detail to exemplary embodiments of the disclosure. While the disclosure will be described in conjunction with the exemplary embodiments, it will be understood that it is not intended to limit the disclosure to those embodiments. To the contrary, it is intended to cover alternatives, modifications, and equivalents as may be included within the spirit and scope of the disclosure as defined by the appended claims. Standard techniques well known in the art or the techniques specifically described below were utilized.

EXAMPLES

Example 1: The CAseq Process

While recent efforts have leveraged long-read sequencing platforms to perform isoform sequencing from single-cell gene expression samples, their workflows have heretofore suffered from poor throughput and substantial sequencing artifacts, with only ~35-50% of reads passing filter, equating to 300,000 sequenced transcripts per flowcell (~$650-800). In certain aspects, the instant disclosure provides the “CAseq” process, which enables high-throughput full-transcript sequencing from 10× single-cell gene expression samples, for example on the recently updated Sequel II platform from Pacific Biosciences (PacBio®). Use of the CAseq process of the disclosure allows for reduction of the fraction of sequencing artifacts observed to <10%, while also allowing for boosting of full length sequencing output to ~25M full-length transcripts per flowcell. To accomplish this, a family of dU-containing primers have been designed, for amplifying and appending 15 base pair (bp) complementary sequences to a full-length cDNA library, for multiplex ligation. To address a major source of artifactual sequences, the exemplified process uses biotinylated primers, to enable purification of full-length cDNA amplicons. To drive efficient multiplexing assembly and mitigate improper ligation events, the 15 bp complementary sequences as exemplified herein were designed to have minimal similarity by ensuring that all sequences be at least 11 hamming distance units apart from one another (Buschmann, T. Bioconductor version: Release (3.11). DOI: 10.18129/B9.bioc.DNABarcodes). A further design consideration was to ensure generation of 15-20 kb multiplexed arrays, the current optimal length for balancing output and base calling accuracy for the Sequel II. Appropriately sized libraries are constructed by programing the number of assembled fragments based off of the size distribution of cDNA. Analysis pipelines are also prepared to process and integrate the multiplexed long-read and the single-cell gene expression data.

Figure 2B:
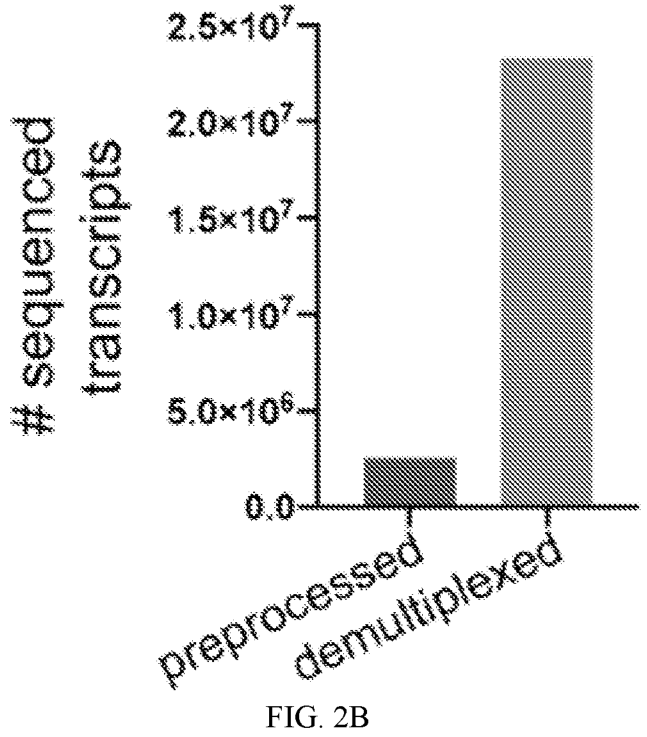
Figure 3A:
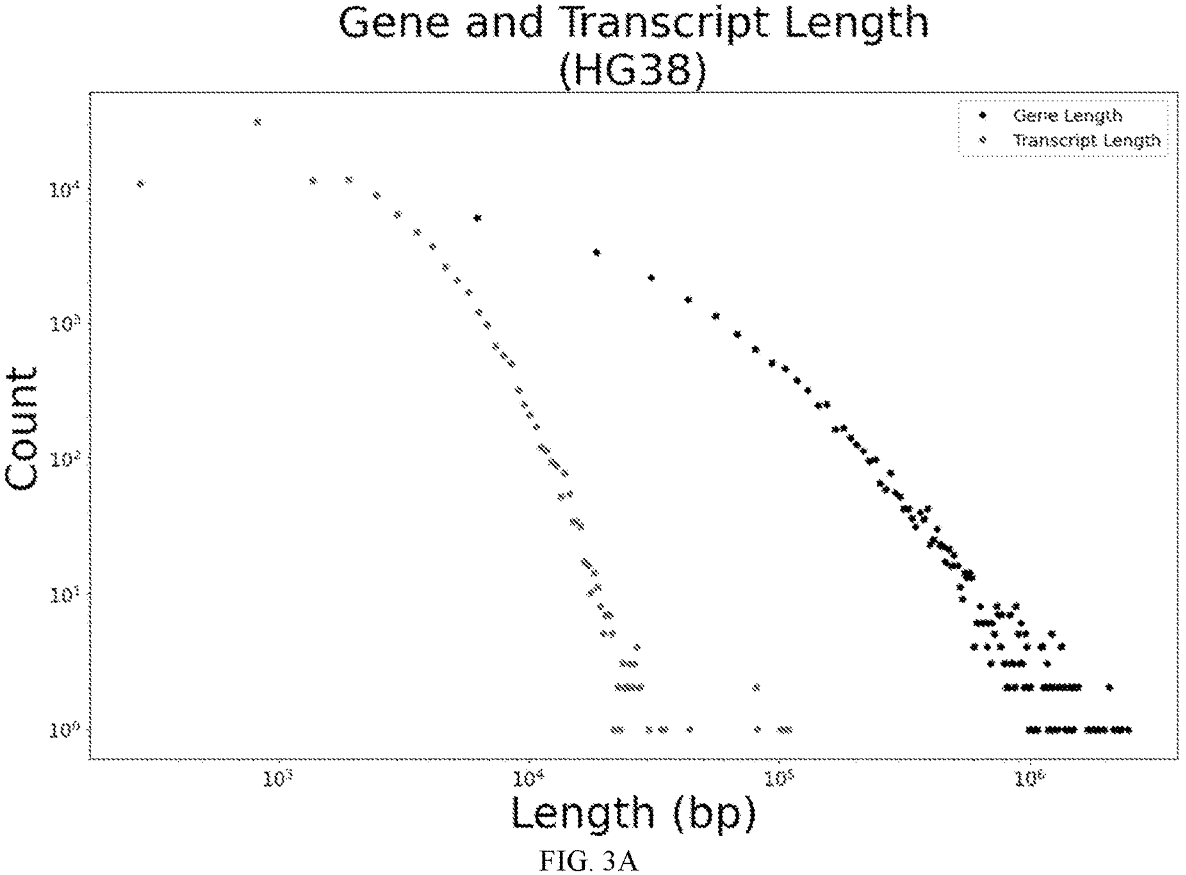
FIGS. 3A and 3B show distributions of gene and transcript lengths across the human genome, relevant to resolving the full sequence content of the chimeric arrays of the instant disclosure in a manner that makes use of the structure present in such chimeric arrays.
Figure 3B:
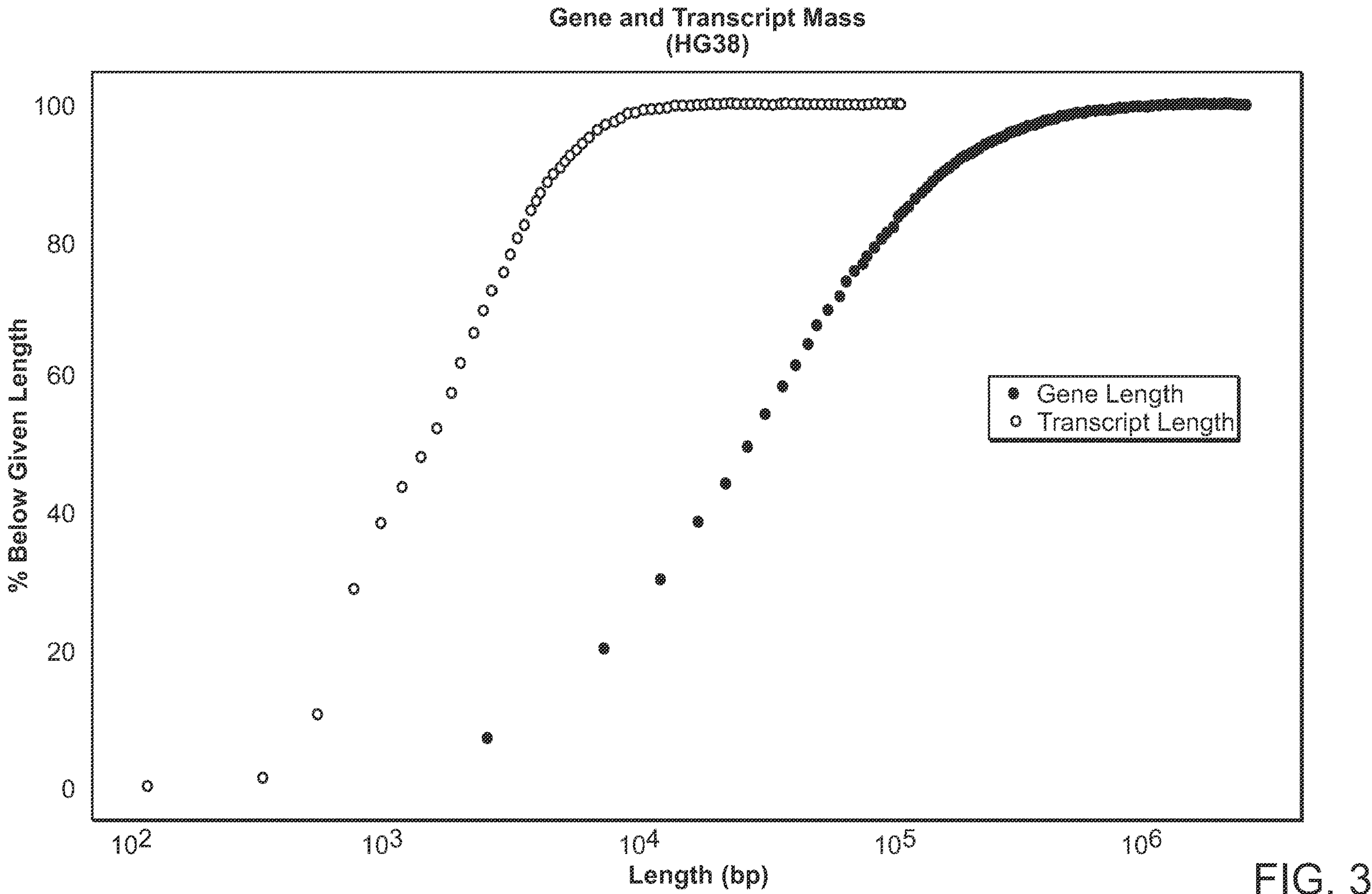
Figure 4:
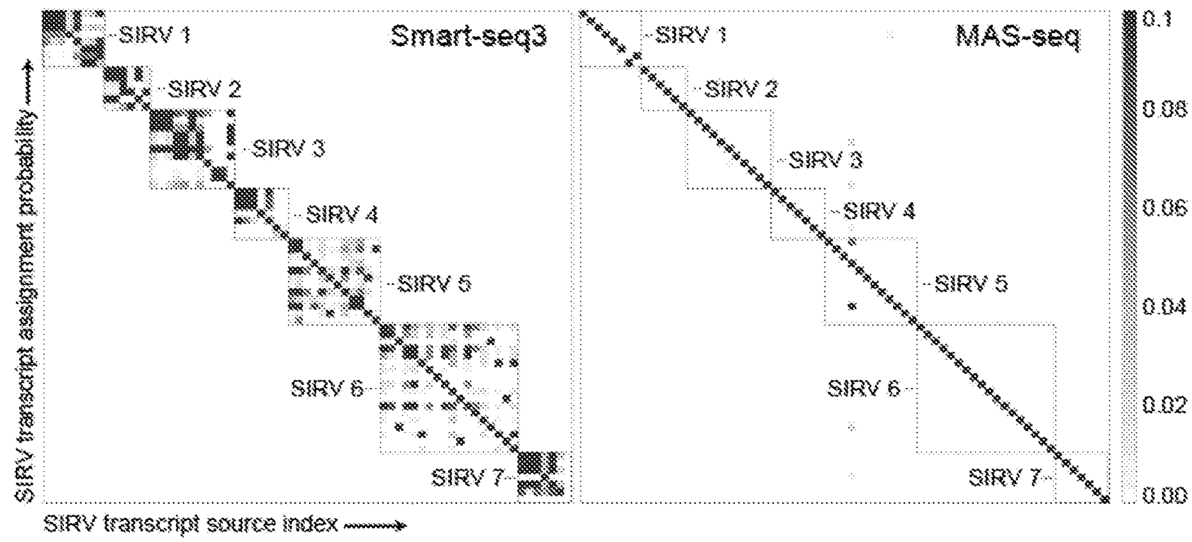
FIG. 4 shows a confusion matrix comparison of the extant "Smart-seq3" process for long read sequence analysis and the presently disclosed chimeric amplicon array sequencing analysis, when each were performed upon Spike-In RNA Variants (SIRVs). SIRVs are divided into seven SIRV genes (SIRV1-SIRV7) which are alternatively spliced similar to human genes. Transcript groups for each gene are indicated by the square outlined regions. Shaded squares indicate similarities between data. The diagonal (top-left to bottom-right) indicates self-similarity for SIRV transcripts. Data produced with Smart-seq3 were observed to have difficulty distinguishing individual transcripts for each SIRV gene, whereas data produced by the presently disclosed chimeric amplicon array sequencing method and analysis was almost completely mapped back to the SIRV transcript from which it was sequenced.
Figure 6:
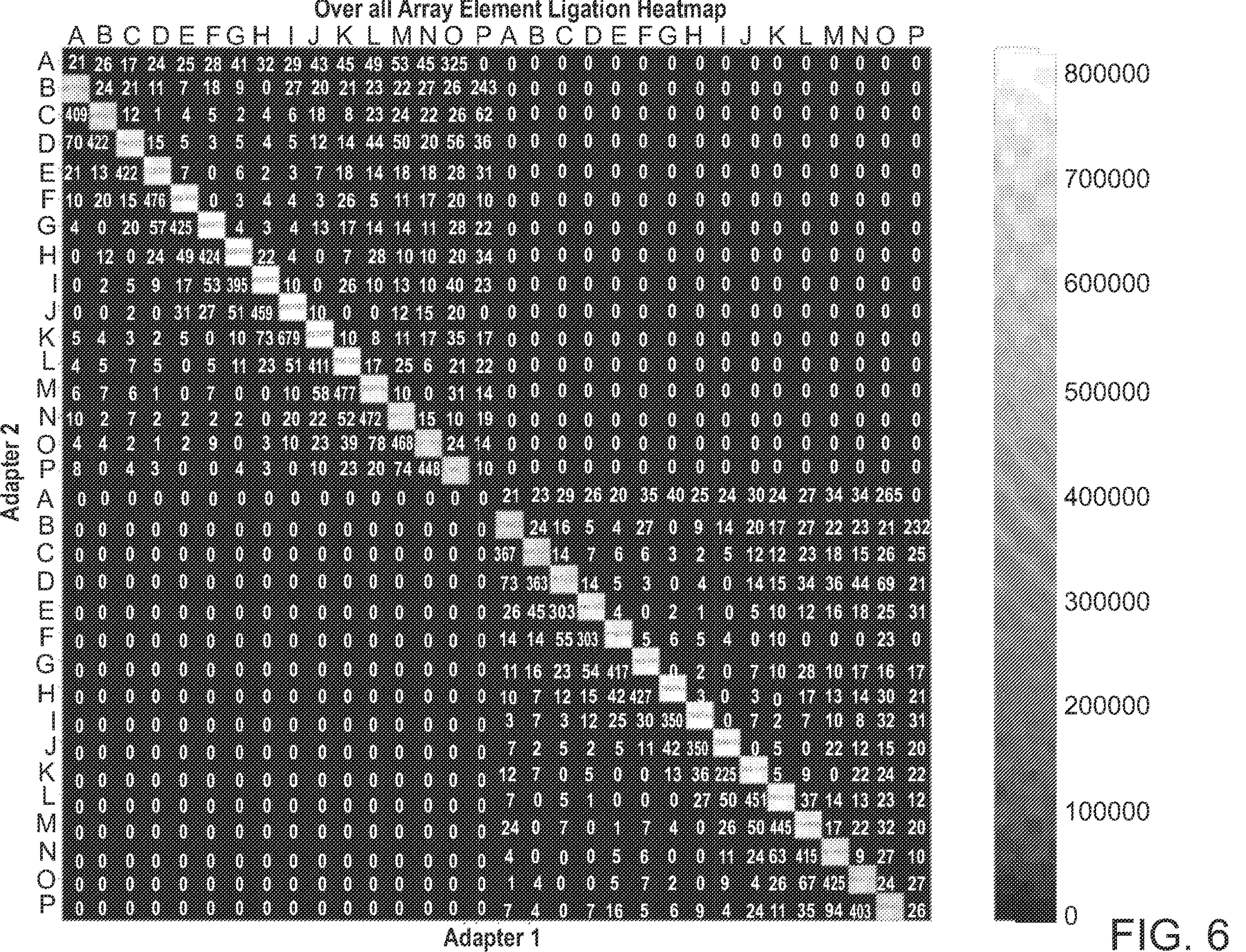
FIG. 6 shows a heatmap of adapter ligations in a human T-cell sample prepared with the presently disclosed chimeric amplicon array sequencing method. Counts indicate the number of ligations from the overhang adapter indicated in each column to the overhang adapter indicated in each row. Reverse complemented sequences are indicated by the ' symbol. In this particular library, the array size was 15 and the expected ligation order was A->B->C->D->E->F->G->H->I->J->K->L->M->N->O->P. The high counts along the diagonal (shifted down one) indicate extremely high rates of expected ligations across the entire prepared library. The break in the center is where the plot switches orientation (to show reverse-complemented ligations separately). Most counts in squares not on the "hot diagonal" are zero, and even the highest counts in squares indicating unexpected detected ligations are at most three orders of magnitude less than counts in the "hot diagonal".
Figure 9A:
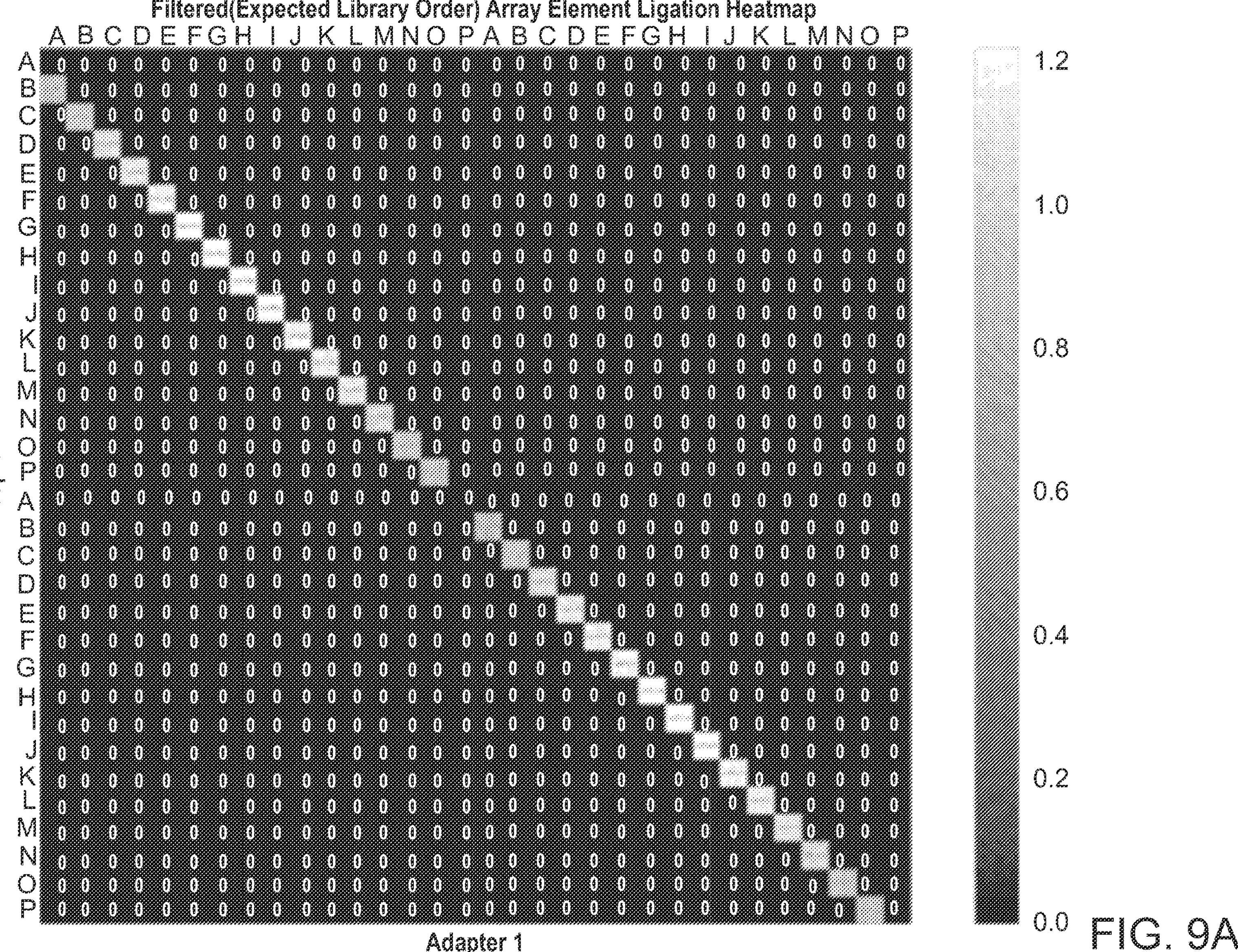
FIGS. 9A and 9B show heatmaps of high-quality and low-quality adapter ligations, respectively, for chimeric amplicon arrays prepared and analyzed by the methods of the instant disclosure.
Figure 9B:
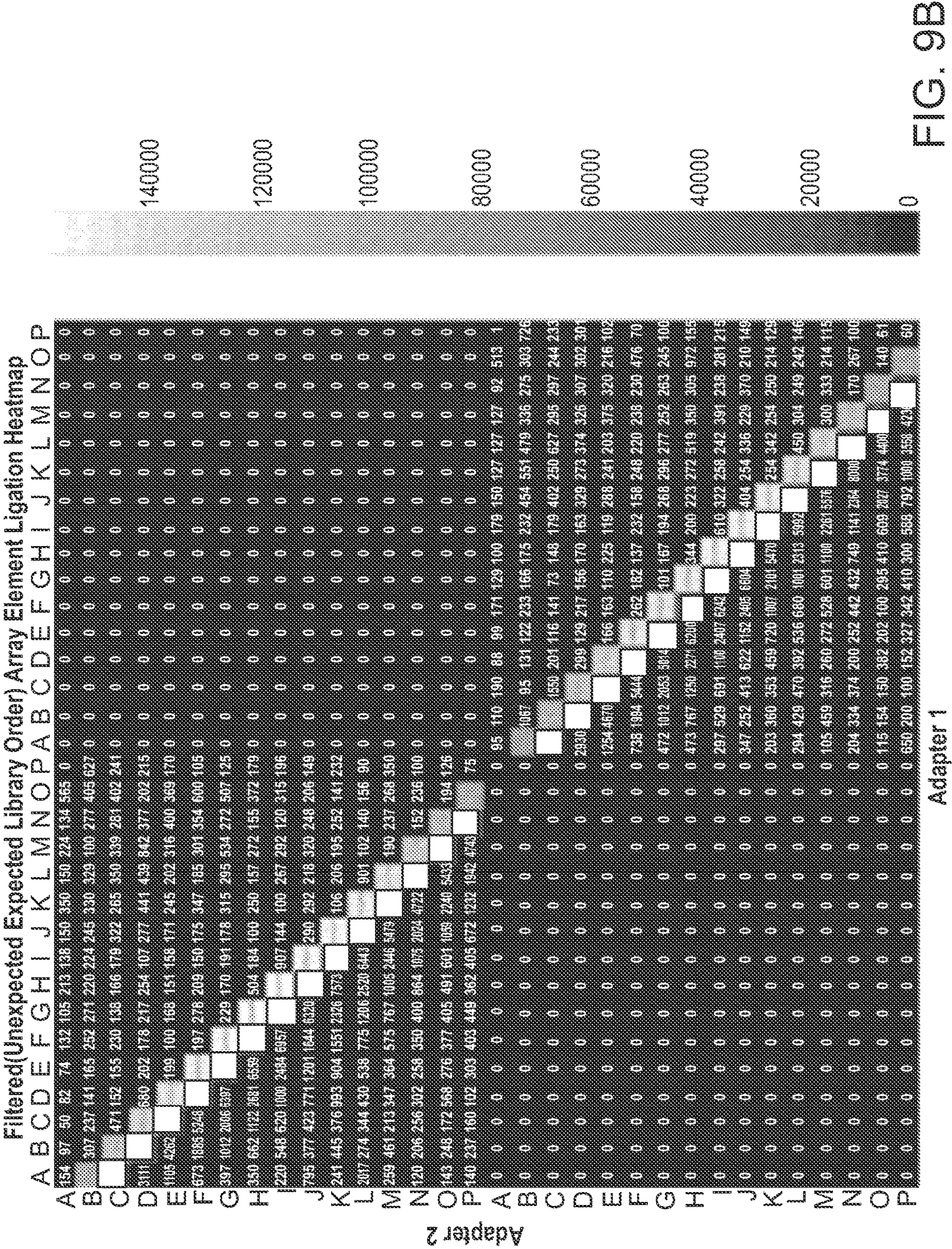
Figures 10A, 10B:
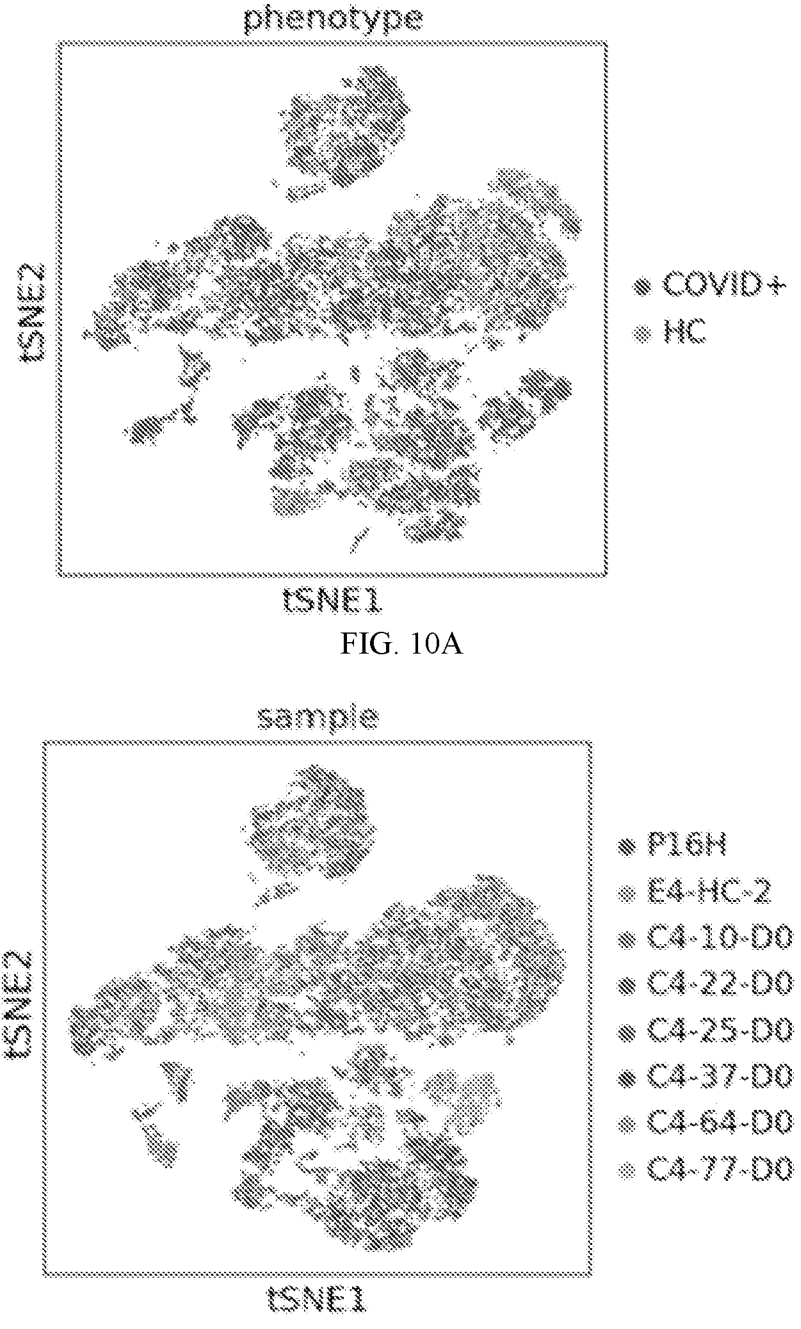
FIGS. 10A to 10D show t-distributed Stochastic Neighbor Embedding (t-SNE) plots that present a clustering assessment of transcript data obtained from comparisons performed between COVID-19 patients and healthy controls (HC), which identified striking transcriptional differences in the monocyte compartment between healthy patients and those with mild and severe COVID-19. The t-SNE plots are derived from assessment of blood samples from healthy and COVID-19 patients, which demonstrate how short-read digital gene expression data can be supplemented with gene isoform information obtained via the CAseq process disclosed herein.
Figure 10C:
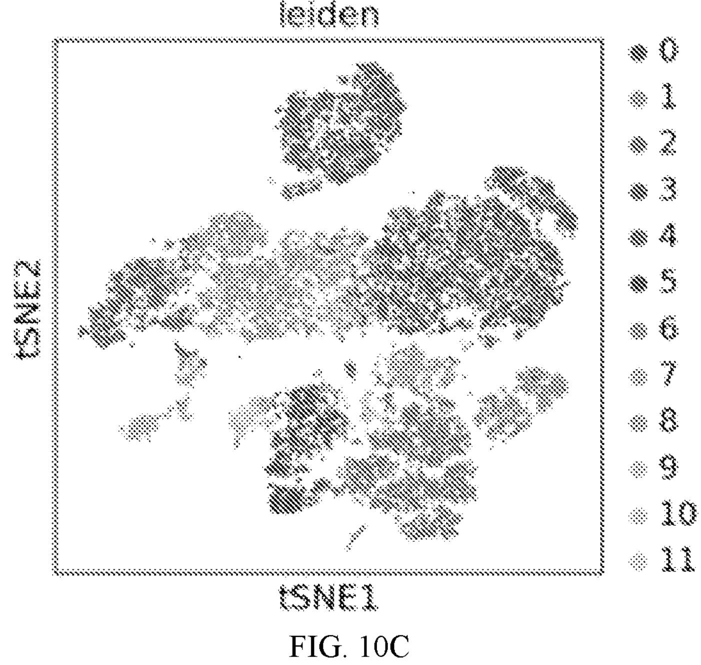
Figure 10D:
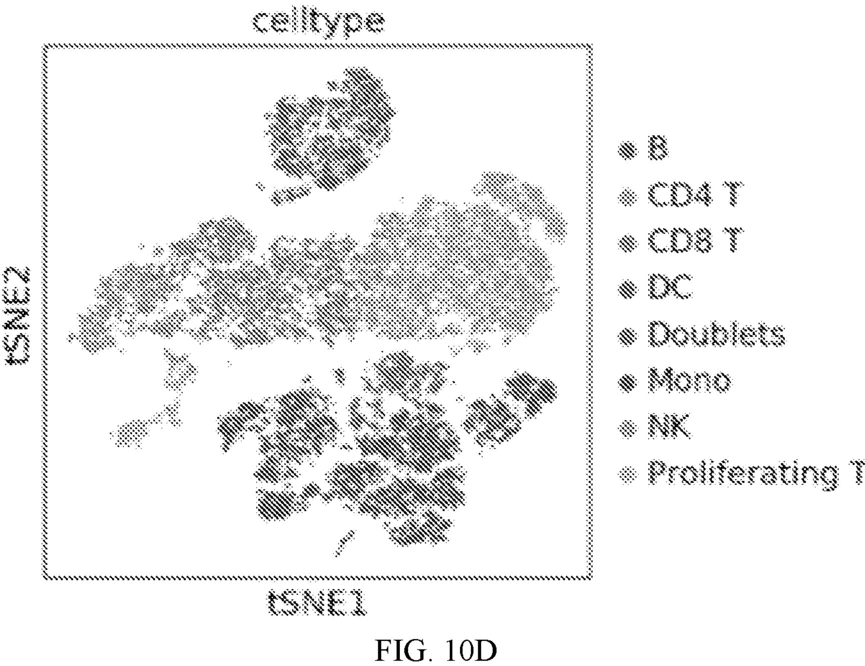
Figure 11A:
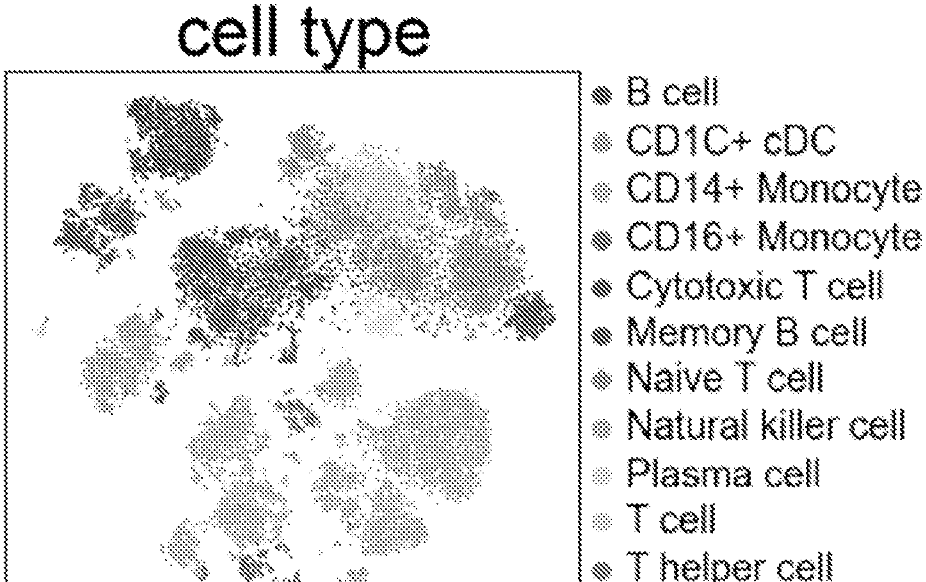
FIGS. 11A to 11C show results obtained from a peripheral blood mononuclear cell (PBMC) sample.
Figure 11B:
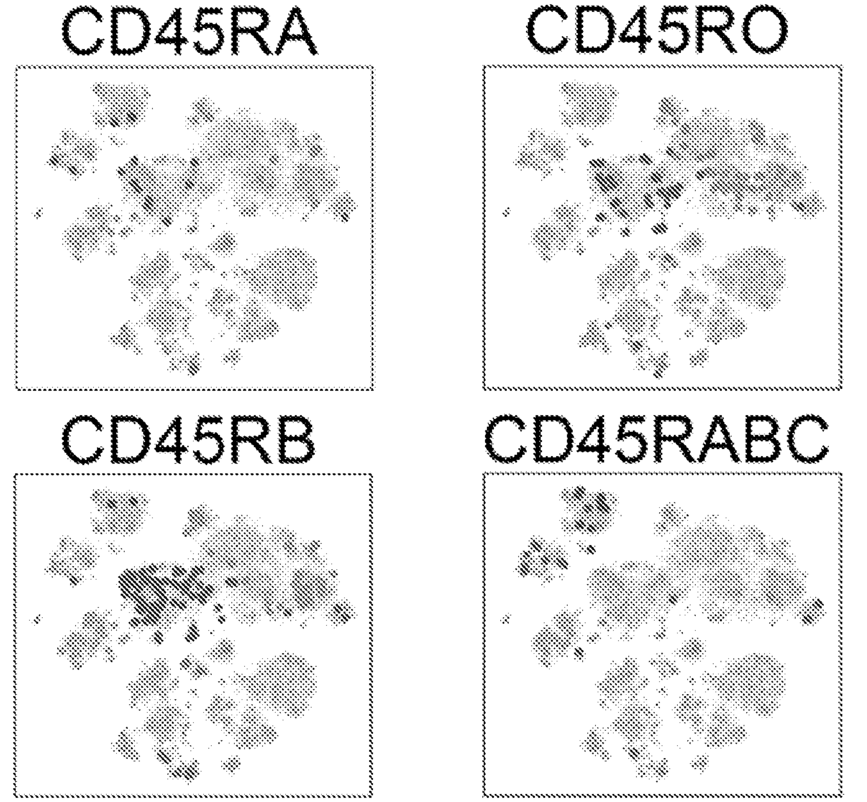
Figure 11C:
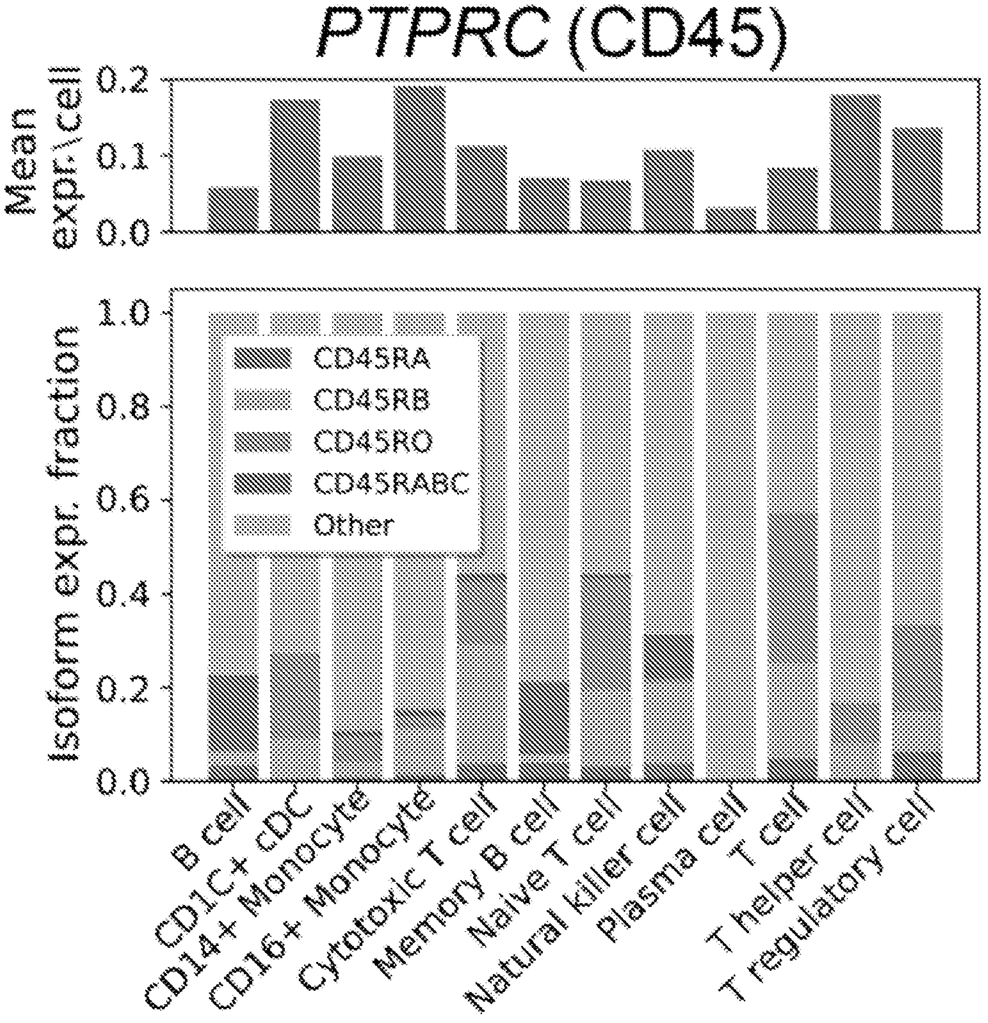

Example 2: CAseq Efficiently Produced Linear Chimeric Arrays in a Pilot Study In a pilot CAseq run, an eight fragment multiplexed assembly from a cDNA library having an average fragment size of 1.2 kb was performed, which resulted in an ~10 kb multiplexed fragment upon ligation (FIG. 2A). The multiplexed library was sequenced on a Sequel II, which resulted in a total of ~2.5M reads, with ~23M transcripts after demultiplexing, which represented approximately a 9-fold increase in throughput (FIG. 2B). Analysis of the demultiplexed reads confirmed a similar size distribution to the original cDNA library (FIG. 2A).

While the exemplified cDNA library size distribution allowed for effective linear chimeric arrays to be formed, it is further contemplated that a size selection can also be performed upon an input nucleic acid library (e.g., via electrophoretic or other separation of an input nucleic acid library, prior to performance of the chimeric array ligation process), which under certain circumstances is expected to increase effective sequence yields from chimeric arrays, particularly where individual read lengths are in the megabases, the total number of arrayed distinct sequences is high, and/or the original distribution of nucleic acid size ranges is disperse.

Example 3: Enhancement of CAseq Read Yields Via Improved Data Annotation, Demultiplexing and Segmentation Methods Initial processing of the chimeric amplicon arrays of the instant disclosure employed an extant circular consensus sequencing (CCS) corrected high fidelity long reads (HiFi reads) process with an iterative adapter finding strategy based on extant genomic read alignment software. This process was identified as sub-optimal for extraction of sequence data from the long reads of the instant chimeric amplicon arrays, and development of improved methods for analysis of CAseq reads was commenced. An improved CAseq read analysis process termed "Longbow" was thereby designed, which involved statistical sequence annotation, demultiplexing, and segmentation of chimeric amplicon array sequencing reads via implementation of the following:

(1) Annotation of chimeric amplicon array sequencing data using one or more statistical annotation models (e.g., a profile hidden Markov model having multiple linked submodels) to identify amplicon array sequences and transitions between them, the one or more statistical annotation models including: (a) a generative statistical alignment model for recognizing a priori expected nucleic acid sequences (i.e. adapter sequences) interspersed throughout a chimeric amplicon array sequencing read; (b) a random statistical alignment model for recognizing sequences not known a priori (e.g. cDNA transcript sequences) or from a dictionary of sequences so large as to merit different considerations at a later processing step (e.g. single cell barcode sequences, unique molecular identifiers), where transitions are placed at the termini of each model and disallowed within internal positions in the adapter sequence model;

(2) Iterative applications of the statistical annotation models of step (1) above to each long read in both forward and reverse-complement orientations, with determination of maximum a posteriori state path Final per-read model selection decided by evaluating the model with the greatest log likelihood value, thereby demultiplexing the chimeric amplicon array sequencing reads; and (3) Segmentation of chimeric amplicon array sequencing reads at sites identified by performance of steps (1) and (2) above.

The above-disclosed "Longbow" process was further identified as useful for quality control and for enhancing sequence data yields from the chimeric amplicon arrays of the instant disclosure, at least in view of applications to: (1) identifying and removing sequence reads that are actually of low quality from a population of reads initially identified by Circular Consensus Sequencing (CCS) software as purportedly high quality; (2) rescuing high quality sequence reads from a population of reads initially identified by Circular Consensus Sequencing (CCS) software as purportedly of unusable quality; and (3) approximating the quality of newly identified high quality reads from the "Longbow" process. Each such application is considered in additional detail below.

For identifying potentially low-quality data from Chimeric Amplicon Array Sequencing of the instant disclosure, the method includes: (a) applying the Longbow model (as described above) to Chimeric Amplicon Array Sequencing reads that have been identified by the sequencer as high-quality (thereby labeling each nucleotide in each of these reads with the library adapter sequence from which it originated); (b) merging equal adjacent Longbow nucleotide labels into regions that comprise the entirety of the labeled section; and (c) iterating over all labeled reads and identifying any reads that have labeled sections that do not occur in the order in the expected order as per the library preparation. Excluded from this are reads that begin after the first expected segment but whose remaining sections are in order, as well as reads that end before the final expected segment but whose prior sections are all in order, and a combination of these cases. Reads that do not conform to the expected library are deemed low quality.

To identify high quality sequencing data from a subset reported by the sequencer as low quality and unusable, the method involves: (a) identifying data (i.e. reads) that the sequencer reports as of unusable quality. Such unusable quality data are determined either by the Circular Consensus Sequencing software assigning the data a very low read quality score (including but not limited to values below zero, values between zero and 0.5, and values between 0.5 and 1.0), or by the Circular Consensus Sequencing software assigning the read to any category other than "ZMWs pass filters"; (b) applying the Longbow model (as described above) to these reads of unusable quality, thereby labeling each nucleotide in each of these reads with the library adapter sequence from which it originated; (c) merging equal adjacent Longbow nucleotide labels into regions that comprise the entirety of the labeled section; and (d) iterating over all labeled reads and identifying any reads that have labeled sections in the order in which they are expected to appear as per the library preparation, including reads that begin after the first expected segment but whose remaining sections are in order, as well as reads that end before the final expected segment but whose prior sections are in order, and any combination of these cases. Such reads conform to the expected library preparation, which indicates that the reads are of high enough quality for further analysis. While the preceding process has been exemplified for application to unusable data such as that assigned a read quality of less than 0.99, or assigned any category other than "ZMWs pass filters", by the Circular Consensus Sequencing software, it is expressly noted that this process can also be applied to any read or population of reads of any purported quality.

For approximating the quality of newly identified high quality reads of the Longbow process, the method includes: (a) for each labeled section in each newly identified high quality read, compute the alignment score between the nucleotides in the labeled section and the expected sequence for that section. This alignment score can be computed directly using dynamic programming algorithms, such as the Smith-Waterman or Needleman-Wunsch algorithms, or directly by computing the Levenshtein distance between the labeled section and the expected sequence and subtracting that distance from the length of the expected sequence; (b) divide this alignment score by the best possible alignment score (which can be obtained by computing the alignment score between the expected sequence and itself) to obtain the quality for each section; and (c) sum all alignment scores computed in (a) to get the overall alignment score. Sum all best possible alignment scores computed in (b) to get the overall best alignment score. The ratio of the overall alignment score to the overall best alignment score is the estimated quality for the read.

Example 4: Implementation of CAseq in a Scalable Single-Cell Isoform Sequencing Workflow for Assessment of COVID-19 Patient Samples Resolution of gene isoform composition from single-cell gene expression studies has previously not been possible. Alternative splicing is a core regulatory process that modulates structure and function of resident proteins through differential exon splicing during transcript maturation. Gene isoforms resulting from alternative splicing have been shown to play central roles in mediating cellular signaling and function (Baralle and Giudice. *Nat Rev Mol Cell Biol* 18: 437-451). Beyond cellular development and homeostatic maintenance, gene isoforms have been implicated in multiple pathologies with hallmark isoforms being linked to multiple disease states or aberrant splicing driving tumor progression and resistance (Kim et al. *Pflugers Arch—Eur J Physiol* 470: 995-1016; Scotti and Swanson. *Nat Rev Genet* 17: 19-32). The inability to effectively capture isoform composition at single-cell resolution highlights a critical deficit in the capacity of previously described methods to effectively characterize heterogeneous biological systems.

In the current example, the CAseq process of the instant disclosure is employed to perform high-throughput isoform sequencing on single-cell gene expression samples. Pipelines for processing and integrating the isoform and single-cell gene expression data are developed using art-recognized analysis tools. Gene panels are also developed, for targeted isoform sequencing. COVID-19 patients are assessed, to characterize both the immune response and infected tissues.

COVID-19 symptoms arise, in part, due to a hyperactive immune response to SARS-CoV-2 infection. CAseq is used in the current example upon COVID-19 samples (derived from an ongoing single-cell genomic study of the immune compartment from blood of 300 COVID-19 patients and tissues from ~10 autopsies), with the goal of discovering differentially expressed isoforms in immune cell clusters associated with severity of disease.

An initial set of (non-CAseq) pilot data has identified striking transcriptional differences in the monocyte compartment between healthy patients and those with mild and severe COVID-19 (FIGS. 10A to 10D). Isoform analyses are focused upon, but not limited to, genes related to inflammation and monocyte activation pathways (see doi.org/10.1093/nar/gky401 and doi.org/10.1038/s41467-019-11076-1). To increase power of isoform analyses, Leiden clusters are grouped together to enable more robust statistical comparisons of differential isoform composition between clusters. Comparing SARS-CoV2 infected samples to healthy control patients, differences of gene expression and the role of alternative splicing were characterized. Reconstruction of the SARS-CoV2 transcriptome is expected to be insightful, as SARS-CoV2 has been shown to utilize a complex discontinuous process of transcription from its genome, making short-read sequencing particularly ill-suited to resolve viral gene expression. To shed light on potential transcriptional dynamics over the course of infection, potential associations with viral transcript composition and quantity in infected cells are thereby investigated.

Example 5: Mitochondrial Lineage Tracing from Single-Cell Gene Expression Samples Intratumor heterogeneity and clonal evolution are the driving forces enabling tumor progression and therapeutic resistance. The capacity to track clonal dynamics is crucial to understanding how tumors are evolving in the face of treatment. Recent approaches have demonstrated that mitochondrial mutations can serve as markers to infer clonal identity (Ludwig et al. *Cell* 176: 1325-1339). Such approaches are, in part, reliant on the fact that mitochondrial genomes incur mutations at a much higher rate (10-100×) as compared to the nuclear genome and are highly represented in the sequencing data. Due to coverage limitations from art-recognized short-read single-cell gene expression workflows, researchers have previously relied upon single-cell ATAC (Assay for Transposase Accessible Chromatin) sequencing to provide uniform and sufficient coverage of the mitochondrial genome necessary for clonal inference. In the current example, the CAseq approach of the instant disclosure is applied to perform targeted long-read sequencing of full mitochondrial transcripts from single-cell gene expression samples, thereby enabling the integration of clonal identity with gene expression samples. Current mitochondrial lineage tracing bioinformatic pipelines are applied and adapted to work with full-length transcript data, with benchmarking performed against current art-recognized methods. Patient tumor samples are then assessed using the instant CAseq process, to uncover clonal dynamics over the course of therapy. The ability to extract clonal information via CAseq-enabled targeted long-read sequencing of full mitochondrial transcripts provides a linking of clonality with gene expression from the same sample. Such coordinated assessment of clonality and gene expression dramatically enhances the study of clonal evolution in tumors over the course of progression and therapeutic resistance.

Example 6: Optimization of Mitochondrial Transcript Capture and Multiplexed Ligation from Single-Cell Gene Expression Samples Until now, single-cell gene expression workflows have been insufficient to capture allelic information to an extent that would allow for robust reconstruction of clonal relationships from individual cells. This has represented an immense lost opportunity, as the capacity to uncover clonal relationships from widely used single-cell gene expression data would promote profound insights, enabling linkages between gene expression state, clonality, and cell fate to be identified. To address the low coverage that has thus far hampered clonal reconstruction from single-cell gene expression samples, CAseq as disclosed herein is also targeted to obtain full-length mitochondrial transcript sequence information. High-efficiency sequencing of mitochondrial transcripts is accomplished by performing targeted amplification of the 13 genes expressed from the mitochondria using multiplexing primers as described elsewhere herein. To ensure the optimal multiplexed array length of 15-20 kb, balancing sequencing output and fidelity, the number of assembled fragments is established in consideration of the length distribution of the mitochondrial cDNA pool. Once sequenced, the full-length transcripts are demultiplexed and filtered for mapping and base quality. Reads passing filter are used to quantify coverage of the mitochondrial genome. Existing mitochondrial lineage tracing pipelines are also adapted to use full-length mitochondrial transcripts for reconstruction of clonal relationships.

Example 7: Benchmarking of Full-Length Mitochondrial Transcript Lineage Tracing

To validate full-length mitochondrial transcript lineage tracing, the ability to reconstruct clonal relationships from a HeLa cell line population harboring stably integrated DNA barcodes is quantified, which can serve to establish ground truths for clonal identity. Specifically, cells tagged with the ClonMapper expressed barcode system (a previously developed system that enables clonal identification through single-cell RNA sequencing) are employed. In addition, the methods described in Ludwig et al. (*Cell* 176: 1325-1339) are performed on a parallel sample of the barcoded population, and measurements related to specificity and recall are calculated for assignment of clonal identity and compared.

The CAseq process disclosed herein accordingly provides a critical advancement in the field of sequencing, as it enables sequencing throughput and read lengths heretofore unattainable by existing platforms. Further, the instant CAseq process is highly adaptable and can be easily specialized to capture genetic features of interest. The implementations of CAseq described in the instant disclosure are provided as new platforms for discovery, with broad applicability to many fields of science. The instant CAseq approach has the capacity to co-evolve with long-read platforms, serving to further boost their molecular output as their read lengths continue to increase.

REFERENCES

1. I. Gupta et al., Single-cell isoform RNA sequencing characterizes isoforms in thousands of cerebellar cells. *Nat Biotechnol.* 36: 1197-1202 (2018).
2. R. Volden et al., Improving nanopore read accuracy with the R2C2 method enables the sequencing of highly multiplexed full-length single-cell cDNA. *Proc Natl Acad Sci USA* 115: 9726-9731 (2018).
3. M. Singh et al., High-throughput targeted long-read single cell sequencing reveals the clonal and transcriptional landscape of lymphocytes. *Nat Commun.* 10: 3120 (2019).

All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

One skilled in the art would readily appreciate that the present disclosure is well adapted to carry out the objects and obtain the ends and advantages mentioned, as well as those inherent therein. The methods and compositions described herein as presently representative of preferred embodiments are exemplary and are not intended as limitations on the scope of the disclosure. Changes therein and other uses will occur to those skilled in the art, which are encompassed within the spirit of the disclosure, are defined by the scope of the claims.

In addition, where features or aspects of the disclosure are described in terms of Markush groups or other grouping of alternatives, those skilled in the art will recognize that the disclosure is also thereby described in terms of any individual member or subgroup of members of the Markush group or other group.

The use of the terms "a" and "an" and "the" and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Embodiments of this disclosure are described herein, including the best mode known to the inventors for carrying out the disclosed invention. Variations of those embodiments may become apparent to those of ordinary skill in the art upon reading the foregoing description.

The disclosure illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present disclosure provides preferred embodiments, optional features, modification and variation of the concepts herein disclosed may be resorted to by those skilled in the art, and that such modifications and variations are considered to be within the scope of this disclosure as defined by the description and the appended claims.

It will be readily apparent to one skilled in the art that varying substitutions and modifications can be made to the invention disclosed herein without departing from the scope and spirit of the invention. Thus, such additional embodiments are within the scope of the present disclosure and the following claims. The present disclosure teaches one skilled in the art to test various combinations and/or substitutions of chemical modifications described herein toward generating conjugates possessing improved contrast, diagnostic and/or imaging activity. Therefore, the specific embodiments described herein are not limiting and one skilled in the art can readily appreciate that specific combinations of the modifications described herein can be tested without undue experimentation toward identifying conjugates possessing improved contrast, diagnostic and/or imaging activity.

The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context. Those skilled in the art will recognize, or be able to ascertain using no more than routine experimentation, many equivalents to the specific embodiments of the disclosure described herein. Such equivalents are intended to be encompassed by the following claims.

We claim:

1. A method for preparing a nucleic acid assembly, the method comprising:

(i) obtaining a plurality of input nucleic acid sequences, wherein each input nucleic acid sequence within the plurality of input nucleic acid sequences is of approximately 30 kilobases in length or shorter;

(ii) attaching one or more adapter sequences to each of the plurality of input nucleic acid sequences, wherein at least one of the one or more adapter sequences comprises an internal dU on one strand, thereby generating a population of adapted nucleic acid sequences;

(iii) contacting the population of adapted nucleic acid sequences with an enzyme capable of generating single-stranded ends on at least one end of each adapted nucleic acid sequence within the population of adapted nucleic acid sequences, thereby forming a population of nucleic acid sequences having single-stranded ends; and (iv) contacting the population of nucleic acid sequences having single-stranded ends with a ligase, thereby forming the nucleic acid assembly.

2. The method of claim 1, wherein the nucleic acid assembly has a length of at least 20 kilobases.

3. The method of claim 1, wherein each input nucleic acid sequence within the plurality of input nucleic acid sequences is of approximately 0.5 to 20 kilobases in length.

4. The method of claim 1, wherein the plurality of input nucleic acid sequences is obtained from one or more cDNA libraries.

5. The method of claim 1, wherein step (ii) further comprises:

contacting the plurality of input nucleic acid sequences with paired amplification primers, wherein at least one primer within the paired amplification primers comprises the adapter sequence comprising the internal dU on one strand; and performing at least one round of amplification to generate the population of adapted nucleic acid sequences.

6. The method of claim 5, wherein the at least one primer within the paired amplification primers is biotinylated.

7. The method of claim 1, wherein the enzyme capable of generating the single-stranded ends comprises: Uracil DNA glycosylase in an enzyme cocktail with Endonuclease VIII.

8. The method of claim 1, wherein an adapter sequence portion of the one or more adapter sequences is 5-30 base pairs in length, and wherein the one or more adapter sequences comprise, from 5' to 3', the adapter sequence portion, a dU nucleotide, and a target nucleic acid sequence portion.

9. The method of claim 1, wherein:

at least one of the one or more adapter sequences further comprises a sequence selected from the group consisting of SEQ ID NOs: 1-18.

10. A method for preparing a nucleic acid assembly, the method comprising:

obtaining a plurality of input nucleic acid sequences, wherein each input nucleic acid sequence within the plurality of input nucleic acid sequences is of approximately 300 kilobases in length or shorter;

ii) contacting the plurality of input nucleic acid sequences with an adapter sequence comprising an internal dU on one strand and a ligase, thereby generating a population of adapted nucleic acid sequences;

iii) contacting the population of adapted nucleic acid sequences with Uracil DNA glycosylase and Endonuclease VIII, thereby forming a population of adapted nucleic acid sequences having single-stranded ends; and iv) contacting the population of adapted nucleic acid sequences having single-stranded ends with a ligase, thereby forming a linear nucleic acid assembly.

11. The method of claim 10, wherein each input nucleic acid sequence within the plurality of input nucleic acid sequences is of approximately 30 kilobases in length or shorter.

12. The method of claim 4, wherein the one or more cDNA libraries comprise at least one of: a single-cell cDNA library, a spatial cDNA library, or cDNAs for immune response pathways.

13. The method of claim 1, wherein the nucleic acid assembly that is formed comprises five or more input nucleic acid sequences.

14. The method of claim 1, wherein the plurality of input nucleic acid sequences is obtained from mitochondrial DNA.

15. The method of claim 1, further comprising:

(v) sequencing the nucleic acid assembly using a long-read sequencing platform.

16. The method of claim 1, wherein each of the one or more adapter sequences comprises at least one designated sequence that is complementary with at least one other of the one or more adapter sequences, thereby forming a population of complementary adapter sequences.

17. The method of claim 16, wherein each complementary adapter sequence of the population of complementary adapter sequences is at least 11 hamming distance units apart from all other complementary adapter sequences in the population.

18. A method for preparing and sequencing a nucleic acid assembly comprising an unbiased assembly of input nucleic acid sequences, the method comprising:

obtaining a plurality of input nucleic acid sequences, wherein each input nucleic acid sequence within the plurality of input nucleic acid sequences is of approximately 300 kilobases in length or shorter;

generating a population of adapted nucleic acid sequences by contacting the plurality of input nucleic acid sequences with paired amplification primers, wherein at least one primer within the paired amplification primers comprises an adapter sequence comprising an internal dU on one strand, and performing at least one round of amplification;

forming a population of adapted nucleic acid sequences having single-stranded ends by contacting the population of adapted nucleic acid sequences with Uracil DNA glycosylase and Endonuclease VIII;

forming the nucleic acid assembly by contacting the population of adapted nucleic acid sequences having single-stranded ends with a ligase, thereby preparing the nucleic acid assembly, wherein the nucleic acid assembly comprises an unbiased assembly of the plurality of input nucleic acid sequences; and sequencing the nucleic acid assembly using a long-read sequencing platform, thereby preparing and sequencing the nucleic acid assembly.

19. The method of claim 18, wherein the adapter sequence of one of the paired amplification primers comprises a designated sequence that is complementary with another of the paired amplification primers.

20. The method of claim 1, wherein the at least one of the one or more adapter sequences is attached via a biotinylated primer comprising the internal dU.

* * * * *